United States Patent
Kurisawa et al.

(10) Patent No.: US 10,221,253 B2
(45) Date of Patent: Mar. 5, 2019

(54) PHASE SEPARATED COMPOSITE

(75) Inventors: Motoichi Kurisawa, Singapore (SG); Li Shan Wang, Singapore (SG); Joo Eun Chung, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 13/642,733

(22) PCT Filed: Apr. 21, 2011

(86) PCT No.: PCT/SG2011/000158
§ 371 (c)(1), (2), (4) Date: Oct. 22, 2012

(87) PCT Pub. No.: WO2011/133113
PCT Pub. Date: Oct. 27, 2011

(65) Prior Publication Data
US 2013/0041044 A1    Feb. 14, 2013

(30) Foreign Application Priority Data

Apr. 23, 2010 (SG) ................ 201002882-7

(51) Int. Cl.
| | | |
|---|---|---|
| *C08B 37/08* | (2006.01) | |
| *A61K 47/48* | (2006.01) | |
| *C08H 1/06* | (2006.01) | |
| *C08J 3/075* | (2006.01) | |
| *C08J 3/24* | (2006.01) | |
| *C08L 5/02* | (2006.01) | |
| *C08L 5/08* | (2006.01) | |
| *C08L 71/02* | (2006.01) | |
| *C08L 89/00* | (2006.01) | |
| *C12N 5/00* | (2006.01) | |
| *C08L 89/06* | (2006.01) | |

(52) U.S. Cl.
CPC .... *C08B 37/0072* (2013.01); *A61K 47/48038* (2013.01); *A61K 47/48292* (2013.01); *C08H 1/06* (2013.01); *C08J 3/075* (2013.01); *C08J 3/246* (2013.01); *C08L 5/02* (2013.01); *C08L 5/08* (2013.01); *C08L 71/02* (2013.01); *C08L 89/00* (2013.01); *C12N 5/0068* (2013.01); *C08L 89/06* (2013.01); *C12N 2533/54* (2013.01); *C12N 2533/80* (2013.01); *C12N 2537/10* (2013.01)

(58) Field of Classification Search
CPC ..................................................... A61L 27/52
See application file for complete search history.

(56) References Cited

U.S. PATENT DOCUMENTS

| | | | | |
|---|---|---|---|---|
| 5,639,796 A | * | 6/1997 | Lee | ............... 514/773 |
| 2009/0204227 A1 | | 8/2009 | Derwin et al. | |
| 2009/0305983 A1 | * | 12/2009 | Ying et al. | ................ 514/12 |
| 2010/0074956 A1 | | 3/2010 | Kurisawa | |
| 2012/0276069 A1 | * | 11/2012 | Karperien | ....... A61K 47/48023 424/93.7 |

FOREIGN PATENT DOCUMENTS

| | | |
|---|---|---|
| JP | 2007/297360 | 11/2007 |
| WO | 2006/010066 A2 | 1/2006 |
| WO | 2006/124000 A1 | 11/2006 |
| WO | 2007/097710 A1 | 8/2007 |
| WO | WO 2007097710 A1 * | 8/2007 |
| WO | 2008/095170 A1 | 8/2008 |
| WO | 2009/135029 A2 | 11/2009 |

OTHER PUBLICATIONS

Albrecht et al., "Probing the Role of Multicellular Organization in Three-Dimensional Microenvironments", Nature Methods, 2006, pp. 369-375, vol. 3 No. 5.
Chen et al., "Vascular Endothelial Growth Factor Promotes Cardiomyocyte Differentiation of Embryonic Stem Cells", Am. J. Physiol. Hear. Circ. Physiol., 2006, pp. 1653-1658, vol. 291.
Bannister et al., "A Simple Method for Increasing Hapten Immunogenicity by a Specific Structural Modification of the Carrier", J. Immuno. Methods, 1989, pp. 57-63, vol. 120 No. 1.
Geiger et al., "Environmental sensing through focal adhesions", Mol. Cell Biol., 2009, pp. 21-33 vol. 10.
Bettinger et al., "Engineering substrate topography at the micro- and nanoscale to control cell function", Angew. Chem. Int. Ed., 2009, pp. 5406-5415, vol. 48.
Bhatia et al., "Tissue Engineering at the Micro-Scale", Biomedical Microdevices, 1999, pp. 131-144, vol. 2.
Raoudi et al., "Differential Effects of Hyaluronan and its Fragments on Fibroblasts: Relation to Wound Healing", Wound Rep Reg., 2008, pp. 274-287, vol. 16.

(Continued)

*Primary Examiner* — Kyle A Purdy
(74) *Attorney, Agent, or Firm* — Wolf, Greenfield & Sacks, P.C.

(57) ABSTRACT

A composite is disclosed. The composite comprises a first conjugate of a polymer and a first phenol-containing moiety, and a second conjugate of a gelatin or collagen and a second phenol-containing moiety, wherein the polymer is selected so that the first conjugate is less cell-adhesive than the second conjugate, at least one of the first and second conjugates is crosslinked to form a matrix, and the composite comprises discrete regions that are rich in one of said first and second conjugates. A method of forming such composite is also disclosed. The method comprises mixing precursors for the first and second conjugates in a solution for forming said composite, and dispersing a catalyst in the solution to catalyze crosslinking of at least one of the first and second conjugates to form the matrix. The composite may be used to grow cells.

20 Claims, 10 Drawing Sheets

(56) References Cited

OTHER PUBLICATIONS

Boraldi et al., "Cell-matrix Interactions of in vitro Human Skin Fibroblasts upon Addition of Hyaluronan", Tissue & Cell, 2003, pp. 37-45, vol. 35.
Brandl et al., "Rational Design of Hydrogels for Tissue Engineering: Impact of Physical Factors on Cell Behavior", Biomaterials, 2007, pp. 134-146, vol. 28.
Darr et al., "Synthesis and characterization of Tyramine-based Hyaluronan Hydrogels", J. Mater. Sci., 2009, pp. 33-44, vol. 20.
Chen et al., "Geometric Control of Cell Life and Death", Science, 1997, p. 1425-1428, vol. 276.
Pirone et al., "Strategies for Engineering the Adhesive Microenvironment", J. Mammary. Gland. Biol. Neoplasia., 2004, vol. 9 No. 4 pp. 405-417.
Shapira et al., "Hydrogels for Cardiac Tissue Regeneration", Biomed. Mater. and Eng., 2008, pp. 309-314, vol. 18 No. 4-5.
Nickerson et al., "Some Physical Properties of Crosslinked Gelatin-Maltodextrin Hydrogels", Food Hydrocolloids, 2005, pp. 1072-1079, vol. 20.
Jin et al., "Enzyme-Mediated Fast in situ Formation of Hydrogels from Dextran-Tyramine Conjugates", Biomaterials, 2007, pp. 2791-2800, vol. 18.
Hahn et al., "Photolithographic patterning of polyethylene glycol hydrogels", Biomaterials, 2006, pp. 2519-2524, vol. 27.
Wang et al., "Injectable biodegradable hydrogels with tunable mechanical properties for the stimulation of neurogenesic differentiation of human mesenchymal stem cells in 3D culture", Biomaterials, 2010, pp. 1148-1157, vol. 31.
Hahn et al., "Three-Dimensional Biochemical and Biomechanical Patterning of Hydrogels for Guiding Cell Behavior", Adv. Mater., 2006, pp. 2679-2684, vol. 18.
Peterbauer et al., "Simple and versatile methods for the fabrication of arrays of live mammalian cells", Lab. chip., 2006, pp. 857-863, vol. 6.
Pratt et al., "Synthetic Extracellular Matrices for in Situ tissue Engineering", Biotechnol. and Bioeng., 2004, pp. 27-36, vol. 86, No. 1.
Jia et al., "Prolongation of sciatic nerve blockade by in situ cross-linked hyaluronic acid", Biomaterials, 2004, pp. 4797-4804, vol. 25.
Khetani et al., "Engineering tissues for in vitro applications", Curr. Opin. Biotechnol, 2006, pp. 524-531, vol. 17.
Lee et al., "An injectable enzymatically crosslinked hyaluronic acid-tyramine hydrogel system with independent tuning of mechanical strength and gelation rate", Soft Matter, 2008, pp. 880-887, vol. 4.
Liu et al., "Three-dimensional photopatterning of hydrogels containing living cells", Biomed. Microdevices, 2002, pp. 257-266, vol. 4.
Oudgenoeg et al., "Peroxidase-mediated cross-linking of a tyrosine-containing peptide with ferulic acid", J. Agric. Food Chem., 2001, pp. 2503-2510, vol. 49.
Peng et al., "Hydrogel-elastomer composite biomaterials: 3 Effects of gelatin molecular weight and type on the preparation and physical properties of interpenetrating polymer networks", J. Mater. Sci.: Mater. Med., 2008, pp. 997-1007, vol. 19.
Murata et al., "Photopolymerization-induced phase separation in binary blends of photocurable/linear polymers", Polymer, 2002, pp. 2845-2859, vol. 43.
Schmidt et al., "Mechanistic and molecular investigations on stabilization of horseradish peroxidase C", Anal. Chem., 2002, pp. 3037-3045, vol. 74, No. 13.
"International Search Report and Written Opinion" dated May 24, 2011, in related PCT international application No. PCT/SG2011/000158.
"International Preliminary Report on Patentability" dated Oct. 23, 2012, in related PCT international application No. PCT/SG2011/000158.
Vanderhooft et al., "Rheological Properties of Cross-Linked Hyaluronan-Gelatin Hydrogels for Tissue Engineering", Macromolecular Bioscience, 2009, pp. 20-28, vol. 9, No. 1.
Suri et al., "Photopatterned collagen-hyaluronic acid interpenetrating polymer network hydrogels", Acta Biomaterialia, 2009, pp. 2385-2397, vol. 5, No. 7.
Turgeon et al., "Protein-polysaccharide interactions: phase-ordering kinetics, thermodynamic and structural aspects", Current Opinion in Colloid and Interface Science, 2003, pp. 401-414, vol. 8.
Kurisawa et al., "Injectable biodegradable hydrogels composed of hyaluronic acid-tyramine conjugates for drug delivery and tissue engineering", Chemical Communications, 2005, pp. 4312-4314.
Extended European Search Report dated Sep. 3, 2013 issued in corresponding EP Application No. 11772335.3.
Office Communication dated Jun. 20, 2014 for European Application No. 11 772 335.3.
Japanese Office Action for Application No. JP 2013-506116, dated Jan. 6, 2016.
Notice of Reasons for Rejection in JP Patent Application No. 2013-506116 dated Apr. 2, 2015.
Kamimura, et al., Injectable biodegradable materials based on hyaluronan. Polymer Preprints, Japan. 2004;53(2): 5422-5423.

* cited by examiner

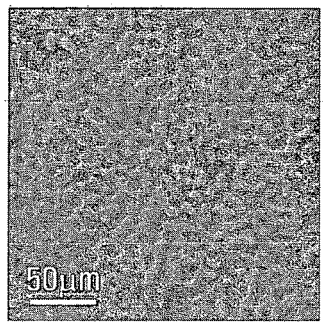 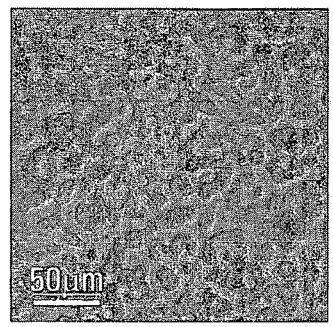 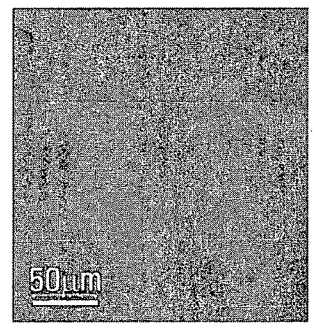
FIG. 11A     FIG. 11B     FIG. 11C
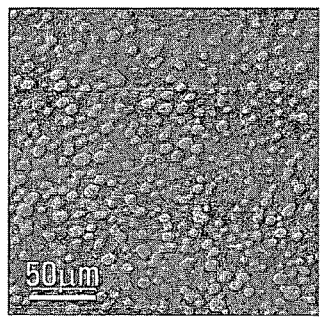 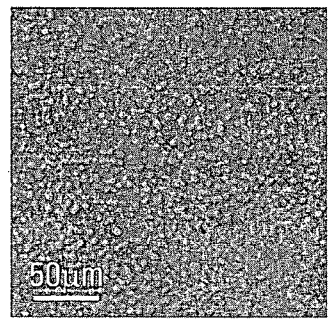 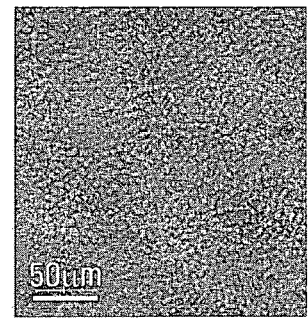
FIG. 11D     FIG. 11E     FIG. 11F

PHASE SEPARATED COMPOSITE

RELATED APPLICATIONS

This application is a U.S. National Stage application based on International Application No. PCT/SG2011/000158, filed on Apr. 21, 2011, which claims benefit of Singapore Patent Application No. 201002882-7, filed on Apr. 23, 2010, each of which is incorporated herein by reference in its entirety.

FIELD

The present invention relates generally to composites and processes for forming composites, and particularly to phase separated composite hydrogels and their formation processes.

BACKGROUND

Composite biomaterials such as composite hydrogels can be useful in a variety of applications including medical and biological applications. For example, they may be useful in therapeutic, tissue engineering, or cell culturing applications. In applications involving living cells, it is desirable to control the microenvironments around the cells, or to be able to modify the microenvironments for various purposes.

It has been reported that composites containing an interpenetrating polymer network (IPN) can be prepared through the formation of photo-crosslinked polymer networks, and the phase structure and morphology of an IPN determine its physical properties. See Peng et al., "Hydrogel-elastomer composite biomaterials: 3. Effects of gelatin molecular weight and type on the preparation and physical properties of interpenetrating polymer networks," *J. Mater. Sci.: Mater. Med.* (2008) 19:997-1007 ("Peng"). Peng notes that most studies have been directed at understanding the impact of alterations in compositions and preparation chemistry on IPN structures, morphologies and properties, and controlling IPN morphology through changes in irradiation intensity, reaction temperatures and chemical structures have also been investigated.

The application of photochemically crosslinked composite hydrogels may be restricted in some cases. For example, 3-dimensional (3D) hydrogels with encapsulated cells are not compatible with photochemical techniques. Using enzymatically controlled crosslinking techniques may be better in some cases to provide implantable hydrogels encapsulated with cells.

Injectable hydrogels are also not compatible with photochemical crosslinking techniques. Enzymatically controlled crosslinking techniques may be better in some cases to provide an injectable composite hydrogel system for injection into a living organism.

SUMMARY

In accordance with an aspect of the present invention, there is provided a composite comprising: a first conjugate of a polymer and a first phenol-containing moiety; and a second conjugate of a gelatin or collagen and a second phenol-containing moiety; wherein the polymer is selected so that the first conjugate is less cell-adhesive than the second conjugate, at least one of the first and second conjugates is crosslinked to form a matrix, and the composite comprises discrete regions that are rich in one of the first and second conjugates.

In accordance with a further aspect of the present invention, there is provided a method of forming the composite as described above comprising: mixing precursors for the first conjugate and second conjugates in a solution for forming the composite; and dispersing a catalyst in the solution to catalyze crosslinking of at least one of the first and second conjugates to form the matrix.

In accordance with another aspect of the present invention, there is provided a composite comprising: a polymer; and a gelatin or collagen; wherein at least one of the polymer and the gelatin or collagen is conjugated with a phenol-containing moiety, the polymer is less cell-adhesive than the gelatin or collagen, the at least one of the polymer and the gelatin or collagen is crosslinked to form a matrix, and the composite comprises discrete regions that are rich in one of the polymer and the gelatin or collagen.

In accordance with a further aspect of the present invention, there is provided a method of forming the composite as described above comprising: mixing the polymer and the gelatin or collagen in a solution for forming the composite, wherein the at least one of the polymer and the gelatin or collagen is conjugated with the phenol-containing moiety; and dispersing a catalyst in the solution to catalyze crosslinking of at least one of the polymer and the gelatin or collagen to form the matrix.

Other aspects, features, and embodiments of the present invention will become apparent to those of ordinary skill in the art upon in view of the following description of specific embodiments of the invention in conjunction with the accompanying figures.

BRIEF DESCRIPTION OF THE DRAWINGS

In the figures, which illustrate, by way of example only, embodiments of the present invention:

FIGS. 11A, 11B, 11C, 11D, 11E and 11F are confocal images depicting the phase separated structures of another different sample Gtn-HPA/HA-Tyr composite hydrogels;

DETAILED DESCRIPTION

Figure 1:
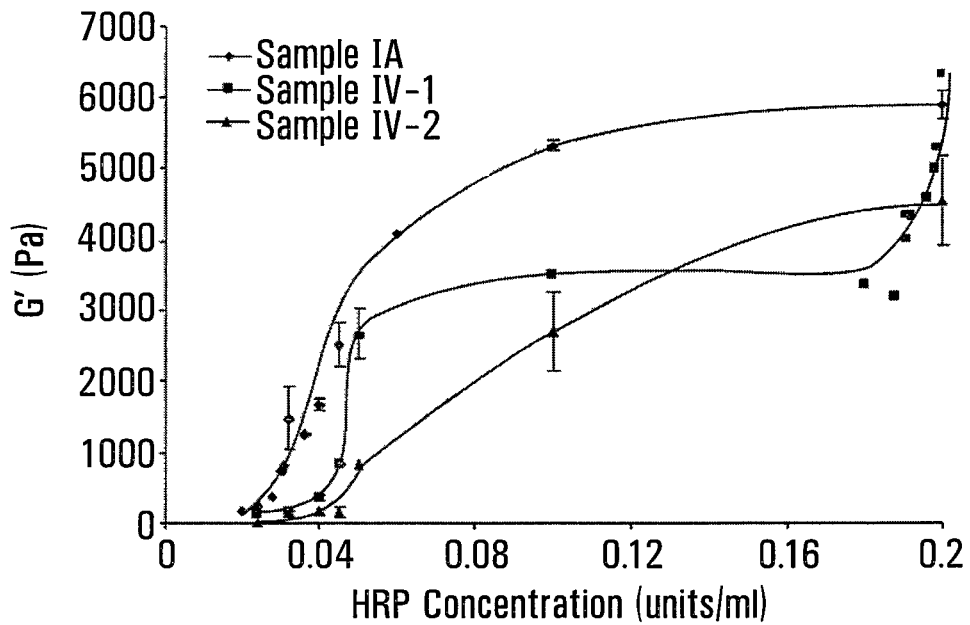
FIGS. 1 and 2 are line graphs respectively depicting stiffness and gelation time of Gtn-HPA/HA-Tyr composite hydrogels prepared at a fixed concentration of $H_2O_2$ according to exemplary embodiments of the present invention.

A composite includes a first conjugate and a second conjugate. In one embodiment, the first conjugate is formed of a polymer and a first moiety, preferably a phenol-containing moiety. The second conjugate is formed of a gelatin or collagen and a second moiety, preferably a phenol-containing moiety. The composite may be in the form of a composite hydrogel. As can be understood, a hydrogel includes a polymeric matrix, which can absorb a liquid such as water. As used herein, a hydrogel may refer to either the polymeric matrix with any absorbed liquid, or the polymeric matrix in its dry state (i.e. without absorbed liquid).

As used herein, a conjugate may include at least two components, which are bound together via at least one chemical bond such as a covalent bond, or a non-covalent bond such as an ionic bond, and a hydrogen bond.

The polymer of the first conjugate is selected so that the first conjugate is less cell-adhesive than the second conjugate. In selected embodiments, the first conjugate is nonadhesive to cells. Cellular adhesion involves binding of a cell to a surface of a material. A material is less cell-adhesive if cells tend to have a lower affinity to bind with the material. A material is considered nonadhesive to cells when cells do not tend to bind with the material. A less cell-adhesive material may not contain a cationic charge or a ligand such as a RGD peptide sequence. The adhesiveness of a material to cells can be measured by culturing cells on the material surface for a period of time and observing whether the cultured cells adhere to the surface. For example, after seeding the cells on the material, the material is incubated for a predetermined period of time. The culture medium is then replaced by fresh medium, after which cell adhesiveness to the material is measured by any applicable methods known to a skilled person in the art.

In selected embodiments, the polymer in the first conjugate may be a hyaluronic acid (HA). In some embodiments, the polymer may be a poly(ethylene glycol) (PEG). In some embodiments, the polymer may be a dextran. The polymer may be itself a conjugate. Suitable polymers may include aldehyde-, carboxyl-, amino-, or succinimide-terminated poly(ethylene glycol)s, aldehyde- or amino-derivatized hyaluronic acids, hyaluronic acid aminoacetylaldehyde diethylacetal conjugates, cyclotriphosphazene core phenoxymethyl(methylhydrazono)dendrimers, thiophosphoryl core phenoxymethyl(methylhydrazono)dendrimers, aldehyde-, carboxyl-, amino- or succinimide-derivatized dextran, or the like.

The phenol-containing moieties in the conjugates may be any suitable moieties that can provide crosslinkable phenol groups for crosslinking the conjugates. The first phenol-containing moiety and the second phenol-containing moiety may be the same or different. For example, tyramine (Tyr), a hydroxyphenylpropionic acid (HPA), a cathechin-based flavonoid, or the like, may be included in a phenol-containing moiety. A phenol-containing moiety may include an HPA and Tyr. In some embodiments, at least one of the first phenol-containing moiety and the second phenol-containing moiety comprises Tyr and/or an HPA. In some embodiments, the phenol-containing moiety in the first conjugate may include tyramine and the phenol-containing moiety in the second conjugate may include a hydroxyphenylpropionic acid (HPA), such as 3,4-hydroxyphenylpropionic acid (3,4-HPA). In some embodiments, the phenol-containing moiety of the first conjugate may include an HPA, such as 3,4-HPA, and/or Tyr such that the first conjugate comprises a conjugate of a polymer and an HPA, and/or a conjugate of the polymer and Tyr. In some embodiments, the phenol-containing moiety of the second conjugate may include an HPA such as 3,4-HPA, and/or Tyr such that the second conjugate comprises a conjugate of gelatin and an HPA and/or a conjugate of gelatin and Tyr.

In selected embodiments, a flavonoid may also be used as a phenol-containing moiety. The flavonoid may be any flavonoid from the general class of molecules derived from a core phenylbenzyl pyrone structure, and may include flavones, isoflavones, flavonols, flavanones, flavan-3-ols, catechins, anthocyanidins and chalcones. In a particular embodiment, the flavonoid may be a catechin or a catechin-based flavonoid. A catechin, or a catechin-based flavonoid is any flavonoid that belongs to the class generally known as catechins (or flavan-3-ol derivatives), and includes catechin and catechin derivatives, including epicatechin, epigallocatechin, catechin, epicatechin gallate and epigallocatechin gallate, and including all possible stereoisomers of catechins or catechin-based flavonoids. In selected particular embodiments, the catechin-based flavonoid is (+)-catechin or (−)-epigallocatechin gallate. In some applications, (−)-epigallocatechin gallate (EGCG) may be selected as it is expected to have the highest activity among the catechin-based flavonoids, possibly due to the trihydroxy B ring and gallate ester moiety at the C3 position of this flavonoid. For example, EGCG may be included as a moiety in the first conjugate.

In one embodiment, the first conjugate is a HA-Tyr conjugate. In another embodiment, the first conjugate is a PEG-EGCG conjugate, a PEG-Tyr conjugate or a PEG-HPA conjugate. In some embodiments, the first conjugate may be a conjugate described in WO/2006/124000 to Zhou et al. published on Nov. 23, 2006 ("Zhou"), the entire contents of which are incorporated herein by reference. In some embodiments, the first conjugate may be a dextran-Tyr or dextran-HPA conjugate. In some embodiments, HA-Tyr conjugate is preferred. The first conjugate may also be unmodified polymers such as PEG, HA and dextran as long as the second conjugate of a gelatin or collagen and a second phenol-containing moiety can form a gel.

In selected embodiments, the second conjugate may include a gelatin. In other embodiments, the second conjugate may include a collagen. In some embodiments, the second conjugate may include a gelatin moiety, which may be a gelatin, or may include a variant or derivative of a gelatin. In some embodiments, the gelatin moiety may contain a gelatin and one or more other components. The second conjugate may also be an unmodified gelatin or collagen as long as the first conjugate of a polymer and a first phenol-containing moiety can form a gel.

The first and second conjugates may include one or more conjugates described in US 2010/0074956 to Kurisawa et al. ("Kurisawa") published on Mar. 25, 2010, the entire contents of which are incorporated herein by reference.

For example, the conjugates may be water soluble and have functional groups that can be conjugated with phenol compounds, with a sufficient degree of conjugation, such as about 6 degree of conjugation, or percentage of conjugation, such as about 90% conjugation. The degree or percentage of conjugation can be conveniently measured by known methods, such as NMR measurements. As examples, for the HA-Tyr conjugate, the degree of conjugation is defined as the number of tyramine conjugated in 100 repeating units of HA, which can be readily determined by NMR measurement. For the gelatin-HPA conjugate, the number of amino functional groups before and after the conjugation is evaluated via NMR measurement. A degree or percentage of conjugation is sufficient if a hydrogel can be formed and/or cell attachment on the hydrogel can be maintained. A suitable conjugate may have functional groups such as hydroxyl, amino, carboxyl or succinimide groups, or the like. Additional suitable conjugates may also include dextran, chitin, chitosan, heparin, or the like. In any particular combination of the conjugates, one of the conjugates should be less cell adhesive than the other conjugate. For instance, in selected embodiments, the second conjugate is selected so that it is cell-adhesive, and the first conjugate is selected so that it is cell-nonadhesive.

In another embodiment, the first conjugate may be formed of a polymer and the second conjugate may be formed of a gelatin or collagen, and only one of the first and second conjugates includes a moiety, which may be a phenol-containing moiety. In this embodiment, the composite comprises a polymer and a gelatin or collagen, wherein at least one of the polymer and the gelatin or collagen is conjugated with a phenol-containing moiety, the polymer is less cell-adhesive than the gelatin or collagen, the at least one of the polymer and the gelatin or collagen is crosslinked to form a matrix, and the composite comprises discrete regions that are rich in one of the polymer and the gelatin or collagen.

At least one of the first and second conjugates in the composite is crosslinked to form a matrix. The molecules of the conjugates may be crosslinked through phenol groups in the conjugates. In some embodiments, molecules of the first conjugate may be crosslinked to form a matrix. In some embodiments, molecules of the second conjugate may be crosslinked to form a matrix. In some embodiments, molecules of both conjugates may be crosslinked to form a matrix. In selected embodiments, for example, when one of the first and the second conjugates does not include a phenol-containing moiety, the matrix may be an interpenetrating polymer network (IPN). In selected embodiments, where both the first and the second conjugates include a phenol-containing moiety, the two polymer networks can be covalently bonded and form a composite hydrogel which is not IPN.

In some embodiments, the composite may include discrete regions (also referred to as "domains") that are rich in one type of conjugate. In some embodiments, the composite may include discrete regions ("domains") that are gelatin- or collagen-rich in the second conjugate. A discrete region is rich in "M" ("M-rich") when the concentration of material "M" in the discrete region is significantly higher than in the adjacent regions surrounding the discrete region. A region is an "M-poor" region when the concentration of "M" in the region is significantly lower than in the adjacent regions. A "M-poor" region may be substantially free of "M". The conjugates in the discrete regions may also be locally crosslinked and form separate hydrogels in the discrete regions. In some embodiments, the conjugates in the discrete regions may also crosslink with the conjugates in adjacent regions.

When the discrete regions have a higher concentration of the first conjugate (i.e. rich in the first conjugate, and poor in the second conjugate), they are less adhesive to cells. When the discrete regions have a higher concentration of the second conjugate (i.e. poor in the first conjugate, and rich in the second conjugate), they are more adhesive to cells. When the polymer is non-adhesive to cells, a polymer-rich region may be non-adhesive to cells. For example, an HA-rich region is generally nonadhesive to cells, and a gelatin-rich or collagen-rich region is generally adhesive to cells.

The discrete regions may have different shapes and may refer to 2-dimensional (2D) or 3-dimensional (3D) regions. The discrete regions may have irregular shapes and may vary in size. When the discrete regions have generally spherical or circular shapes, the size of the discrete regions may be measured by their diameters. The size of a non-spherical, or non-circular, discrete region may refer to the largest length of the region, or may be calculated as the diameter of a circular or spherical reference region that has the same area or volume as the discrete region in question, depending on the application, convenience, or the accuracy required.

The sizes of the discrete domains and the distances between them may be on the order of nanometers to micrometers. In some embodiments, the discrete regions may have an average size of about 10 nm to about 500 μm, such as from about 10 nm to about 100 μm.

The distance (shortest distance) between two adjacent discrete regions can also vary. The average distance between adjacent discrete regions may be about 5 nm to about 500 μm, such as from about 5 nm to about 50 μm.

As can be appreciated, the distances between regions and the sizes of the regions may be measured or estimated for example, by observation from images of the composite, such as confocal images, or by dynamic laser measurement.

As can be understood, the sizes of the discrete regions and the distances between adjacent discrete regions reflect the degree of phase separation in the composite. The composite may be considered to have a phase formed of the first conjugate and a phase formed of the second conjugate. As will be further discussed below, the composite can be formed with different degrees of phase separation. For example, depending on the formation process, the two conjugates could possibly be crosslinked to form an integrated network with no apparent separation between the two phases. The two conjugates may also be crosslinked to form a composite with a phase-separated structure.

Conveniently, the exemplary composite have different regions (separated phases) with different cell-adhesiveness. As will be further described below, the sizes of the discrete regions (domains) and the distances between the regions, in other words, the degree of phase separation, can be conveniently controlled during the formation process. Thus, the exemplary composite can be conveniently adapted to provide different and desired microenvironments for cells.

The composite may further contain other desired additive(s) such as a drug, a protein or a cell, depending on the application. The drug may include a therapeutic protein. For example, interferon, herceptin, or the like may be included in the composite. Non-therapeutic proteins, such as α-amylase, lysozyme, or the like, may also be included in the solution. The cell may comprise a stem cell, such as human mesenchymal stem cell. The amount of other additive(s) may be selected depending on the particular application. It should be noted, however, that the addition of other additive(s) may impact on the mechanical strength (e.g. stiffness) or other properties of the formed composite hydrogel or on the formation process, such as the gelation rate. Thus, depending on which and how much other additive(s) are included, the concentration of the catalyst, such as $H_2O_2$ or horseradish peroxidase (HRP), or both, may need to be adjusted to off-set such impact.

Another exemplary embodiment of the present invention relates to a method of forming a composite as described above. It should be understood that the composite may also be prepared or formed by other methods.

In the exemplary method, precursors for the first and second conjugates are mixed in a solution for forming the composite and a catalyst, or a combination of catalysts, is added and dispersed in the solution to catalyze crosslinking of at least one of the first and second conjugates to form a hydrogel matrix. The crosslinking of the matrix is thus chemically and/or enzymatically initiated.

The precursors may be selected based on the desired conjugates to be crosslinked. The selection of precursors and their preparation, and the crosslinking of the conjugates may be carried out as described in Zhou (described above) and Kurisawa (described above), with or without modification depending on the particular compounds used. In a particular embodiment, the first and second conjugates may be each formed through a carbodiimide/active ester-mediated coupling reaction.

The conjugates may be crosslinked through oxidative coupling of the phenol groups in the conjugates, which may be catalyzed by the presence of a catalyst. In exemplary embodiments, the catalyst may include horseradish peroxidase (HRP) and $H_2O_2$. In selected embodiments, both horseradish peroxidase and $H_2O_2$ may be used. As can be understood, phenols can crosslink through either a C—C linkage between the ortho-carbons of the aromatic ring or a C—O linkage between the ortho-carbon and the phenolic oxygen.

In selected embodiments, the gelation solution contains an effective amount of HRP for crosslinking the conjugates to form the composite hydrogels. The amount of HRP is typically specified or measured in units (U). One unit of HRP is the amount of HRP that catalyses the reaction of 1 μmol of the substrate in 1 minute under the standard conditions. For example, the gelation solution may contain from about 0.01 to about 2.0 units/ml, or from about 0.02 to about 0.2 units/ml, of HRP. The concentration of HRP may also be expressed alternatively in g/ml. For example, HRP may be available in 100 U/mg, in which case the solution may contain from about 0.1 to about 20 μg/ml of HRP, such as from about 0.2 to about 2.0 μg/ml.

The concentration of HRP may be selected in order to reach the gel point at a pre-determined time, as explained in Kurisawa (described above). In some embodiments, an optimal HRP concentration may be selected to achieve the desired stiffness of the composite hydrogel, the desired gelation time and consequently, the desired phase separation where the weight ratio (wt. ratio) of the first and second conjugates and the concentration of $H_2O_2$ are both fixed. For example, the reaction solution may contain about 0.062 units/ml of HRP. While holding the weight ratio of the first and second conjugates and the concentration of $H_2O_2$ constant, a higher HRP concentration, for example at above about 0.2 units/ml in one embodiment, can yield a composite hydrogel with higher stiffness, less gelation time and less phase separation. As can be appreciated, varying the HRP concentration can change the gelation rate/speed and the crosslinking efficiency, which may in turn affect the phase separation in the composite hydrogel.

Conveniently, one or more of the catalyst(s) dispersed in the solution may have an amount selected to control the rate of crosslinking to allow one of the conjugates to concentrate in the discrete regions, so as to control the degree of phase separation, such as reflected in the sizes of the discrete regions and the distances between the discrete regions. For example, the HRP concentration may be selected to control the rate of crosslinking to obtain discrete regions with sizes in a pre-selected range.

For this purpose, a correlation between the concentration of the catalyst, such as HRP, in the solution and the sizes of the discrete regions formed of one of the two phases may be obtained, such as through pre-testing. The amount or concentration of the catalyst can then be selected to control the degree of phase separation based on this correlation. The correlation may be expressed as a graph, a table, an equation, or in a database.

Also conveniently, when both HRP and $H_2O_2$ are used, the concentration of $H_2O_2$ in the solution may be selected to control the stiffness of the formed composite. Consequently, both stiffness and the degree of phase separation of the composite may be conveniently controlled by adjusting the concentrations of HRP and $H_2O_2$ in the gelation solution.

In some embodiments, the conjugates may be water-soluble. In different embodiments, the weight ratio of the first conjugate to second conjugate may vary from about 9:1 to about 1:9. In different embodiments, the weight ratio is 9:1, 8:2, 8.5:1.5, or 7:3.

As now can be understood, in an exemplary method, the stiffness of composite may be controlled by varying the concentration of $H_2O_2$, or HRP, or both. The degree of phase separation in the composite may be controlled by adjusting the gelation rate, through selection of an appropriate HRP concentration. In particular, the degree of phase separation can be decreased by increasing HRP concentration.

Without being limited to any specific theory, it is expected that when the gelation rate is fast, the crosslinked molecules have less time to grow in size and to increase their molecular weight. Molecules with smaller molecular weight are expected to be less likely to separate into different phases. Thus, it may be expected that a faster gelation rate can lead to decreased phase separation.

With an exemplary composite described herein, the surface patterns of cell-adhesive regions and cell-nonadhesive regions may be conveniently provided and controlled, without using lithographic processes, or photo-initiated crosslinking. The composite may be used to provide injectable systems or active agent-delivering carriers, and to provide a controlled microenvironment.

To form composite hydrogels with different degrees of phase separation, different conjugate weight ratios and/or different HRP concentrations can be used. In one embodiment, Gln-HPA conjugate, HA-Tyr conjugate, HRP and $H_2O_2$ are mixed to form a Gln-HPA/HA-Tyr composite hydrogel. The Gln-HPA conjugate and HA-Tyr conjugate are respectively dissolved in distilled water prior to the mixing. In one embodiment, the weight ratio Gln-HPA:HA-Tyr=9:1, in another embodiment, the weight ratio Gln-HPA:HA-Tyr=8:2, in another embodiment, the weight ratio Gln-HPA:HA-Tyr=8.5:1.5, in another embodiment, the weight ratio Gln-HPA:HA-Tyr=7.0:3:0. The concentration of HRP ranges from about 0.01 to about 2.0 units/ml or from about 0.02 to about 0.2 units/ml. The concentration of $H_2O_2$ may be range from about 1 mM to about 17 mM, such as 0.175 mM, 0.88 mM, 8.5 mM or 17 mM.

A general scheme for formation of the composite hydrogels is shown in SCHEME I.

Scheme I.

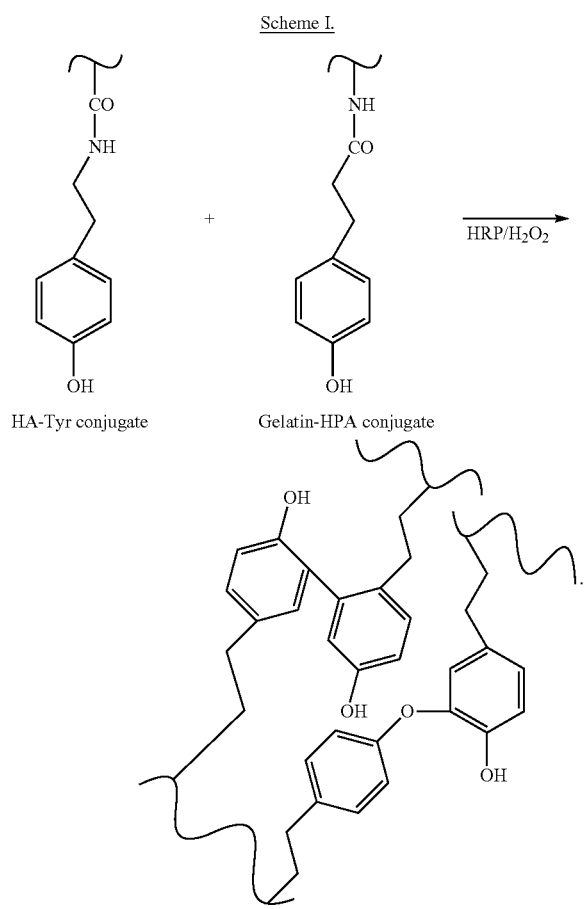

HA-Tyr conjugate    Gelatin-HPA conjugate

Also conveniently, as the degree of phase separation may be controlled without varying the composition or weight ratios of the first and second conjugates in the composite, the composite may be more conveniently formed and may be formed with a wide variety of properties, including different stiffness and different cell-adhesiveness.

The composite may be specifically designed and formed to enhance cell proliferation in the composite, as compared to cell proliferation in hydrogels formed of the second conjugate, such as Gtn-HPA.

In some embodiments, the presence of both cell-adhesive regions and cell-nonadhesive regions can improve cell proliferation in the composite. As a result, even when the stiffness of the composite is relatively low, satisfactory cell proliferation can still be achieved. In comparison, in hydrogels formed of the second conjugation (e.g. Gtn-HPA), a decrease in stiffness can result in decreased cell proliferation.

Rheological methods can be used to study the viscoelastic behavior of a hydrogel. In particular, the stiffness and gelation time of the hydrogel may be measured using oscillatory rheometry, which measures the storage modulus (G', unit=Pa) against the shear strain.

In a gelation process, the values of G' for the formed composite may be obtained over time and when the G' values become substantially constant (i.e. when G' reaches a plateau), it may be expected that crosslinking has been completed. The time from addition of the catalyst(s) to the time of G' reaching the plateau may be considered as the gelation time. The stiffness and gelation time of a composite hydrogels may also vary with the weight ratio of the first and second conjugates in the reaction solution.

In an exemplary embodiment, a Gtn-HPA/HA-Tyr composite hydrogel may have a lower G' as compared to a pure Gtn-HPA hydrogel. When the amounts/concentrations of HRP and $H_2O_2$ in the reaction solution are maintained constant, the stiffness of the composite hydrogel may decrease with increasing percentage of HA-Tyr in the composite hydrogel. The stiffness of the composite hydrogel may also increase with increasing HRP concentration in the reaction solution.

Generally, the gelation time can be expected to be longer when the HRP concentration in the reaction solution is lowered. A similar effect may be expected for $H_2O_2$. A higher HRP concentration can be expected to yield a composite hydrogel with higher stiffness and less gelation time.

Stiffness can also be lowered by increasing $H_2O_2$ concentration. This is most likely due to the deactivation of the HRP by an excess amount of $H_2O_2$.

Confocal images can be used to study the phase separation in the composite hydrogel. To obtain such images, each of the conjugate precursor may be first conjugated with a different fluorophore in order to label discrete domains in the composite hydrogel. Different fluorophores are used in order to provide different colours of excited fluorescence, allowing the observation of different phases in the composite hydrogel. As long as the conjugates with fluorescent molecules do not lower water solubility of the conjugates and pose no restriction on observing the phase separated structure, any fluorophores may be used. For example, in the Gtn-HPA/HA-Tyr composite hydrogel, the Gtn-HPA conjugate is conjugated with Rhodamine while the HA-Tyr conjugate is conjugated with Fluroscein. The fluorophore conjugated precursor may be prepared with or without modifications according to the procedures described in Kurisawa (described above) or other procedures known in the art.

The effect of additional conjugation with fluorophores on the phase separation can be kept to a minimum by optimizing the degree of fluorophore conjugation to less than 0.5%. Methods of determining the degree of fluorophore conjugation are generally well known to those skilled in the art. For example, the degree of fluorophore conjugation may be estimated by comparing the absorbance value of a fluorophore conjugated precursor at a wavelength at which the fluorophore emits fluorescence against a set of standards containing the fluorophore.

In an exemplary embodiment, prior to the formation of the Gtn-HPA/HA-Tyr composite hydrogel, Gtn-HPA is conjugated with Rhodamine and HA-Tyr is conjugated with fluorescein, both to a degree less than 5%.

It can be expected that, at a given conjugate content, at lower concentrations of HRP, discrete domains can form in the composite hydrogel, and the lower the HRP concentration, the larger the domain sizes.

Without being limited to any particular theory, it is expected that there is a correlation between the catalyst (e.g. HRP and/or $H_2O_2$) concentration and the gelation time, and that during the gelation process to form a composite hydrogel, both a phase separation process and the gelation process can occur. A slower gelation rate would mean more time for phase separation, and larger discrete domains can form within the composite. In contrast, a faster gelation rate can result in smaller-sized domains.

The contents of the conjugates (or their precursors in the reaction solution) can also affect phase separation and the resulting phase separated structures. For example, when content of a given conjugate is high (such as >90%), the conjugate is likely to form a crosslinked network throughout the composite. When the content of the given conjugate is low (such as <80%), the conjugate may form discrete domains in the composite, and a slower gelation rate can lead to the formation of larger discrete domains and a faster gelation rate can result in smaller domains, where the domains are distributed in a continuous network formed by the other conjugate.

Thus, it should be noted that varying the percentages (or weight ratio) of the different conjugates in the composite hydrogel can produce different phase-separated structures. This may be at least in part due to the fact that the ratio of the conjugate precursors in the reaction can affect the gelation rate.

Another factor that may affect the gelation rate is the reaction temperature. In exemplary embodiments, the reaction temperature may be varied from about 25° C. to about 37° C.

A further factor that may affect the gelation rate is the molecular weights of the precursors for the conjugates. In selected embodiments, the molecular weights of the precursors may be from about 5 kDa to about 10,000 kDa for HA-Tyr, and about 10 kDa to about 500 kDa for Gtn-HPA. In some embodiments, the molecular weights of the precursors for Gtn-HPA may be from about 80 kDa to about 140 kDa.

However, varying the reaction temperature, the weight ratio of the precursors, and the molecular weights of the precursors can lead to other changes in the resulting composite hydrogel, which may not be desirable. In such cases, it would be convenient to select the values for these parameters based on other considerations, and control the gelation rate by adjusting the concentration of the catalyst such as HRP.

As now can be appreciated, variations and modifications to the exemplary embodiments described herein are possible. For example, more than three types of conjugates may be included in the composite. The first and second conjugates may include other components. For instance, two or more suitable cell-nonadhesive polymers may be included in the first conjugate.

Conveniently, the exemplary composite may be useful in various fields and applications, including biomedical applications, such as therapeutic, tissue engineering, cell culturing applications, or the like. In addition, the composite may be used as an extracellular matrix (ECM) in some applications. The composite may be used to control the microenvironments around cells, or may be conveniently modified to form different microenvironments for various purposes. The composite may be formed in situ, and the reaction solution for forming the composite may be provided as an injectable system for injection into a living body. For example, a mixture of the composite solution and cells may be injected into a site in a human or animal body. In some embodiments, selected composites can be used to culture cells and provide improved cell proliferation, attachment, function control, and long-term viability. Exemplary composites may also be used in or as implants. They may provide implantable hydrogels encapsulated with cells or proteins, or the like, and may be used to regenerate tissues, organs, or the like. They may be used in cell cultivation applications, including cultivation in a controlled 3D environment. They may be used in vivo or in vitro. They may be suitable for primary cell culture. Other uses and applications are also possible as can be understood by those skilled in the art.

As described herein, in some embodiments, cell proliferation (e.g. human foreskin fibroblasts) may be enhanced in the composite hydrogels (e.g. Gtn-HPA/HA-Tyr) with larger domains of the second conjugate (e.g. Gtn-HPA), which can be prepared by selecting an appropriate HRP concentration. Accordingly, the cell growth in the composite hydrogel can be independently controlled by selecting an appropriate HRP concentration. For example, in a method of growing cells in the composite hydrogel, the composite hydrogel is formed from a precursor composite solution containing the first conjugate, the second conjugate and catalyst(s), and the cells are then dispersed in the precursor composite solution. The catalyst(s) concentration in the composite precursor solution is selected to obtain different desired microenvironments for cell growth.

In some embodiments, protein secretion (e.g. albumin secretion from primary rat hepatocytes) may be better maintained in the composite hydrogels (e.g. Gtn-HPA/HA-Tyr) as compared with hydrogels containing the second conjugate alone (e.g. Gtn-HPA). Protein secretion (e.g. albumin secretion from primary rat hepatocytes) may also be enhanced in the composite hydrogels (e.g. Gtn-HPA/HA-Tyr) containing a higher percentage of the first conjugate (e.g. HA-Tyr) as compared with those containing a lower percentage of the first conjugate. Conveniently, composite hydrogels may be used for protein production and a desired amount of protein may be produced at a desired rate by selecting an appropriate composition of the composite.

In an exemplary method of protein production using the composite hydrogel, the composite hydrogel is formed from a precursor composite solution containing the first conjugate, the second conjugate and catalyst(s), and the hepatocytes are dispersed in the precursor composite solution. The catalyst(s) concentration in the composite precursor solution and the composition of the composite hydrogel may be independently selected to obtain desired amount of the protein produced at a desired rate.

The exemplary composite may be formed in situ, and the reaction solution for forming the composite may be injected into a living body so that the gelation will mainly occur within the body. The body may be a tissue, organism, human body, animal body, or another type of living body.

A drug or protein or cells may be added to the reaction solution before gelation and before the solution is injected into the body.

For example, in one embodiment, the reaction solution containing Gtn-HPA, HA-Tyr, HRP and $H_2O_2$ in distilled water is immediately injected into the living body. Depending on the specific application, selected amounts of HRP, $H_2O_2$ and Gtn-HPA:HA-Tyr ratio may be added to form the reaction solution.

Embodiments of the present invention may be advantageously utilized in a wide range of applications, in addition to cell growth, protein production, tissue regeneration, or drug delivery.

Exemplary embodiments of the present invention are further illustrated with the following examples, which are not intended to be limiting.

EXAMPLES

The materials used in the Examples were obtained as follows unless otherwise specified in the specific example.

Gelatin (Gtn) (MW=80-140 kDa, pI=5) and Horseradish peroxidase (HRP, 100 units/mg) were obtained from Wako Pure Chemical Industries™.

Hydrogen peroxide ($H_2O_2$) was obtained from Lancaster™.

3,4-Hydroxyphenylpropionic acid (3,4-HPA), tyramine hydrochloride (Tyr.HCl), N-hydroxysuccinimide (NHS), 1-ethyl-3-(3-dimethylaminopropyl)-carbodiimide hydrochloride (EDC.HCl), Rhodamine B isothiocynate and 5-aminofluorescein were purchased from Sigma-Aldrich™.

Human foreskin fibroblast (HFF1) cells were obtained from ATCC (USA).

Dulbecco's modified eagle medium (DMEM), Hepatozyme medium, fetal bovine serum (FBS) and streptomycin were purchased from Invitrogen™.

Colleagenase and dexamethasone were purchased from Sigma™.

Reporter lysis buffer was purchased from Promega™.

Example I

Example I-A Synthesis of Gtn-HPA Conjugates (Sample IA)

Gtn-HPA conjugates were prepared according to the procedures described in L. Wang et al., "Injectable biodegradable hydrogels with tunable mechanical properties for the stimulation of neurogenesic differentiation of human mesenchymal stem cells in 3D culture," *Biomaterials*, 2010, 31, 1148-57 ("Wang"), the entire contents of which are incorporated herein by reference.

3,4-HPA (3.32 g, 20 mmol) was dissolved in 250 ml of a mixture of distilled water and N,N-dimethylformamide (DMF) (3:2) to form an initial solution. To the initial solution, NHS (3.20 g, 27.8 mmol) and EDC.HCl (3.82 g, 20 mmol) were added. The reaction mixture was stirred at room temperature for 5 hours, and the pH of the mixture was maintained at 4.7. Subsequently, 150 ml of aqueous Gtn solution (6.25 wt. %) was added to the reaction mixture and the mixture thus formed was stirred overnight at room temperature at pH 4.7. The solution was transferred to dialysis tubes with molecular cut-off of 1000 Da. The tubes were dialyzed against 100 mM sodium chloride solution for 2 days: a mixture of distilled water and ethanol (3:1) was used for the first day and distilled water was used for the second day. The purified solution was lyophilized to obtain Gtn-HPA conjugates.

A general reaction route for preparing sample IA is shown in SCHEME II.

SCHEME II.

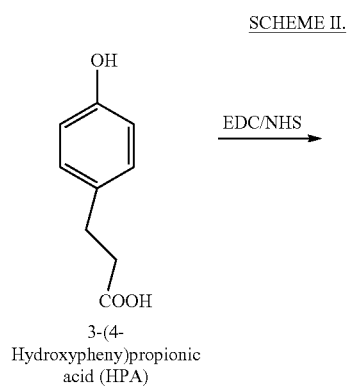

3-(4-Hydroxypheny)propionic acid (HPA)

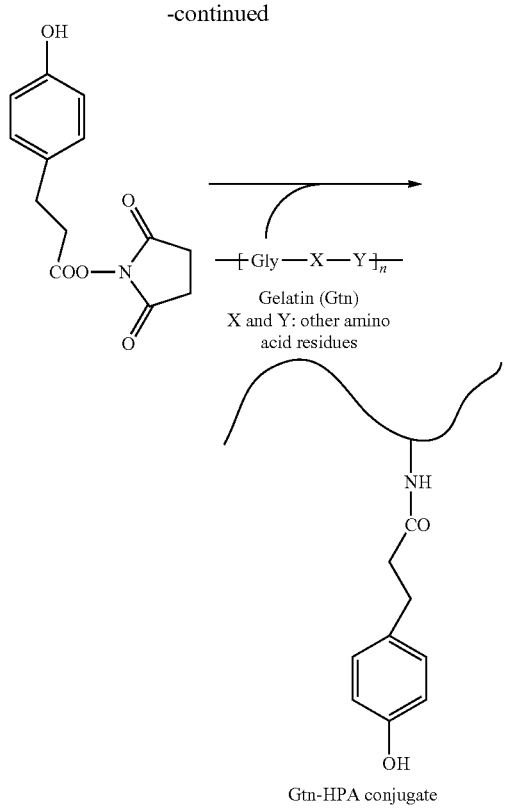

Gtn-HPA conjugate

Example I-B Synthesis of Gtn-HPA-Rhodamine (Gtn-HPA-Rho) Conjugates (Sample IB)

The entire reaction including the dialysis was carried out in the dark. Into an aqueous solution of Gtn-HPA conjugates (1 g) obtained from Example I-A in distilled water, Rhodamine B isothiocynate (1 mg, dissolved in DMSO) was added and the reaction mixture was stirred overnight at room temperature. The solution thus formed was dialyzed in distilled water by using a dialysis membrane (1 kDa molecular weight cut off) for two days. The purified solution was lyophilized to obtain the Gtn-HPA-Rhodamine conjugates. The degree of Rhodamine conjugated was estimated by comparing the absorbance value at 570 nm of 1 mg/ml Rhodamine-conjugated Gtn-HPA solution to a set of Rhodamine standards using Tecan Infinite® M200 microplate reader. The degree of substitution of Rhodamine was 0.3.

Example II Synthesis of HA-Tyr Conjugates (Sample II)

HA-Tyr conjugates were prepared according to the procedures described in F. Lee et al., "An injectable enzymatically crosslinked hyaluronic acid-tyramine hydrogel system with independent tuning of mechanical strength and gelation rate, *Soft Matter* 4, 880-887 (2008) ("Lee"), the entire contents of which are incorporated herein by reference.

HA (1 g, 2.5 mmol) was dissolved in 100 ml of distilled water, forming an initial solution. Tyr.HCl (202 mg, 1.2 mmol) was first added to this solution. EDC.HCl (479 mg, 2.5 mmol) and NHS (290 mg, 2.5 mmol) were then added to initiate the conjugation reaction. As the reaction proceeded, the pH of the mixture was maintained at 4.7 with 0.1 M NaOH. The reaction mixture was stirred overnight at room temperature and then the pH was brought to 7.0. The solution was transferred to dialysis tubes with molecular cut-off of 1000 Da. The tubes were dialyzed against 100 mM sodium chloride solution for 2 days: a mixture of distilled water and ethanol (3:1) was used for the first day and distilled water was used for the next day. The purified solution was lyophilized to obtain HA-Tyr conjugates.

A general reaction route for preparing sample II is shown in SCHEME III.

tated. The filtrate was collected into dialysis tubes with molecular cut-off 3500 Da. The dialysis and lyophilization procedures for Gtn-HPA described in Example I-A above were followed. The degree of aminofluorescein conjugated was estimated by comparing the absorbance value at 490 nm of 1 mg/ml aminofluorescein-conjugated HA-Tyr solution to a set of aminofluorescein standards using Tecan Infinite® M200 microplate reader. The degree of substitution of aminofluorescein was 0.4.

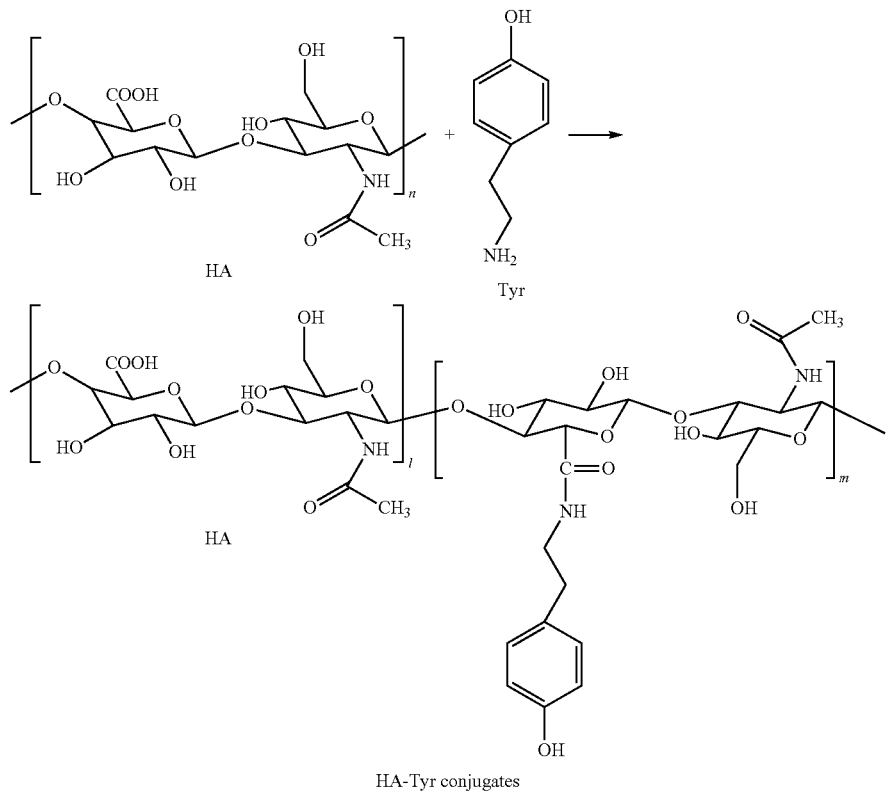

SCHEME III.

HA-Tyr conjugates

Example III Synthesis of HA-Tyr-Fluorescein (HA-Tyr-Flu) Conjugates (Sample III)

HA-Tyr-Fluorescein conjugates were prepared according to the procedures described in Lee (described above).

The entire reaction including the dialysis was carried out in the dark. HA (2 g, 5 mmol) was dissolved in 100 ml of distilled water to form an initial solution. To the initial solution, Tyr.HCl (0.4 g, 2.3 mmol) and 5-aminofluorescein (10 mg, 0.04 mmol in 1 ml DMSO) were added. EDC.HCl (960 mg, 5 mmol) and NHS (580 mg, 5 mmol) were then added and the pH of the mixture was maintained at 4.7 with 0.1 M NaOH. The reaction was stirred overnight at room temperature and was then brought to pH to 7.0. The solution was filtered with grade 1 Whatman™ cellulose filter paper to remove unconjugated aminofluorescein that had precipi-

Example IV Rheological Measurements of Gtn-HPA/HA-Tyr Composite Hydrogels (Samples IV-1, IV-2, IV-3, IV-4)

Rheological measurements of the formation of Gtn-HPA/HA-Tyr composite hydrogels were performed with a HAAKE™ Rheoscope 1 rheometer (Karlsruhe, Germany) using a cone and plate geometry of 35 mm diameter and 0.945° cone angle. The measurements were taken at 37° C. in the dynamic oscillatory mode with a constant deformation of 1% and frequency of 1 Hz. To avoid slippage of samples during the measurement, a roughened glass bottom plate was used.

Solutions of Gtn-HPA and HA-Tyr, as prepared in Examples I-A and II respectively, were prepared by dissolving the respective conjugates in phosphate buffered saline (PBS, pH=7.4), wherein the final concentration of each of the Gtn-HPA and HA-Tyr solutions was 5 wt %. Aqueous solutions containing Gtn-HPA and HA-Tyr in the weight ratio of 9:1 or 8:2 were prepared (5 wt %, 250 µL PBS) by mixing the Gtn-HPA solution with the HA-Tyr solution.

In a representative rheological measurement, a solution of HRP in PBS and a solution of $H_2O_2$ in PBS were added sequentially to an aqueous solution containing Gtn-HPA and HA-Tyr, prepared according to the above paragraph, to form a sample solution. A general reaction scheme to prepare the composite hydrogel is provided in SCHEME I above.

The sample solution was then vortexed and immediately applied to the bottom plate. The upper cone was then lowered to a measurement gap of 0.024 mm and a layer of silicon oil was carefully applied around the cone to prevent solvent evaporation during the measurement. The measurement parameters were determined to be within the linear viscoelastic region in preliminary experiments. A frequency of 1 Hz and a shear strain of 1% were applied to maintain linear viscoelasticity. The measurement was done at 37° C. The G' value and the time taken to reach it (i.e. gelation time) were recorded.

The rheological measurements were repeated, wherein the concentration of HRP ranged from 0.02 units/ml to 0.2 units/ml and the concentration of $H_2O_2$ was either 8.5 mM or 17 mM.

The ingredients of sample Gtn-HPA/HA-Tyr composite hydrogels (samples IV-1, IV-2, IV-3, IV-4) prepared are summarized in TABLE I.

TABLE I

Sample Gtn-HPA/HA-Tyr composite hydrogels (samples IV-1, IV-2, IV-3, IV-4).

| Sample | Gtn-HPA:HA-Tyr (wt. ratio) | $[H_2O_2]$ (mM) |
| --- | --- | --- |
| IV-1 | 9:1 | 8.5 |
| IV-2 | 8:2 | 8.5 |
| IV-3 | 9:1 | 17 |
| IV-4 | 8:2 | 17 |

As a comparison, the G' value and the gelation time for Gtn-HPA hydrogels (sample IA) without addition of HA-Tyr were also measured.

Representative rheological measurement results are shown in FIGS. 1, 2, 3 and 4.

Figure 2:
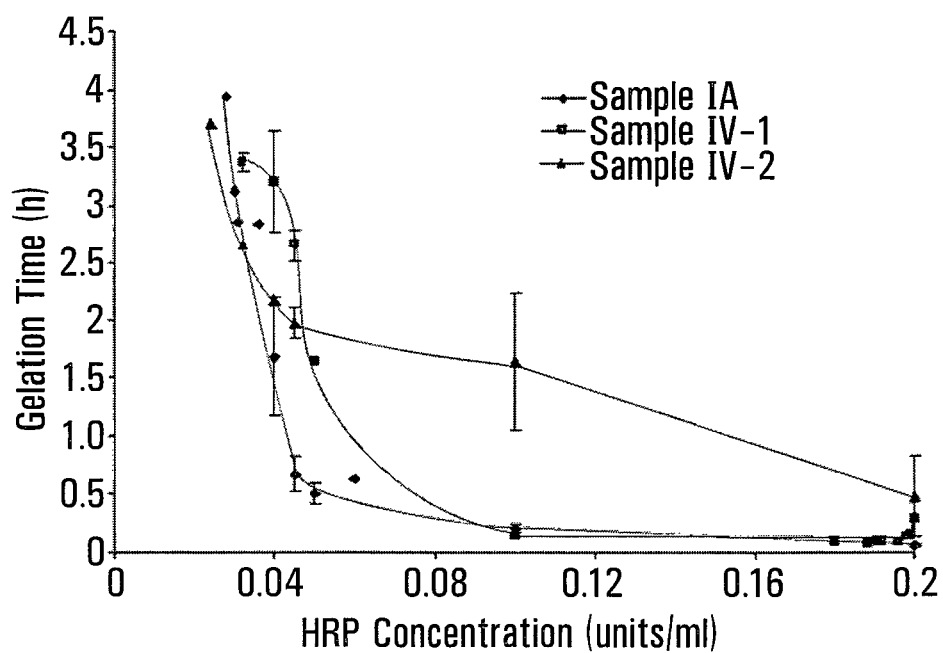

FIG. 1 shows the dependency of stiffness of Gtn-HPA/HA-Tyr composite gels on HRP concentration, which is indicated by the G' values of sample IV-1 and sample IV-2 as a function of HRP concentration at a fixed $H_2O_2$ concentration of 8.5 mM. FIG. 2 shows the dependency of gelation time of Gtn-HPA/HA-Tyr composite gels on HRP concentration, which is indicated by the gelation time of sample IV-1 and sample IV-2 as a function of HRP concentration at a fixed $H_2O_2$ concentration of 8.5 mM.

Figure 3:
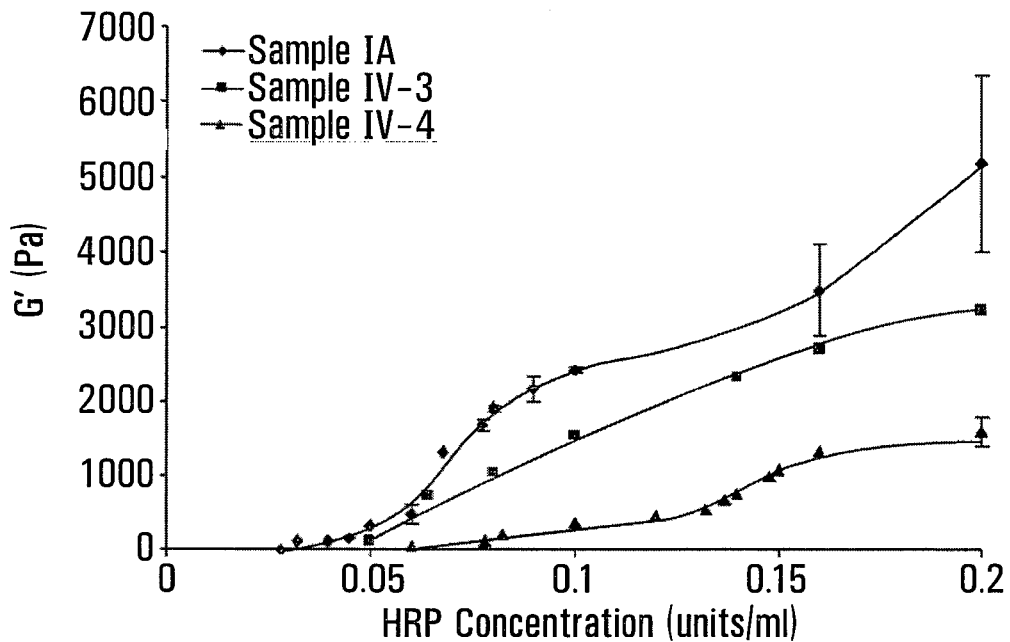
FIGS. 3 and 4 are line graphs respectively depicting stiffness and gelation time of Gtn-HPA/HA-Tyr composite hydrogels prepared at another fixed concentration of $H_2O_2$ according to exemplary embodiments of the present invention.
Figure 4:
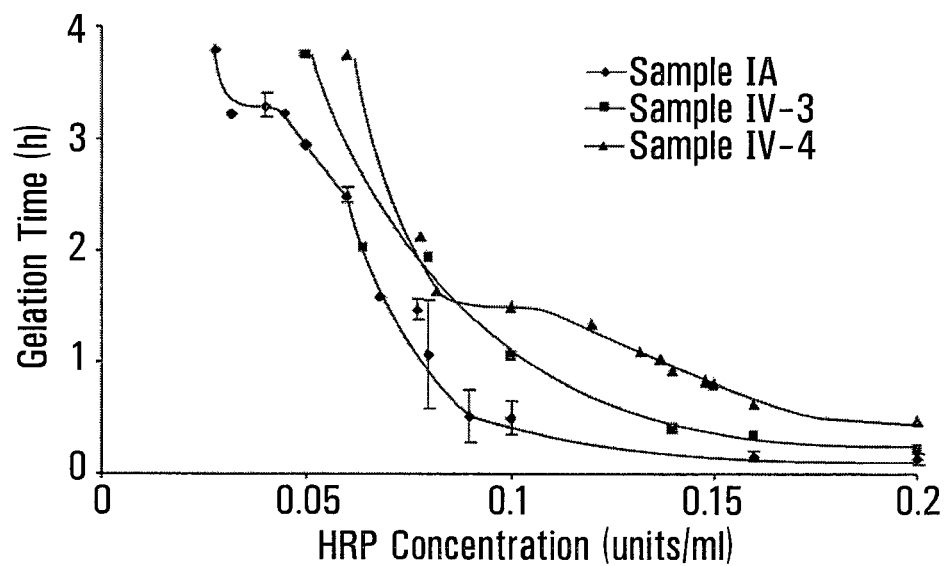
Figure 5A:
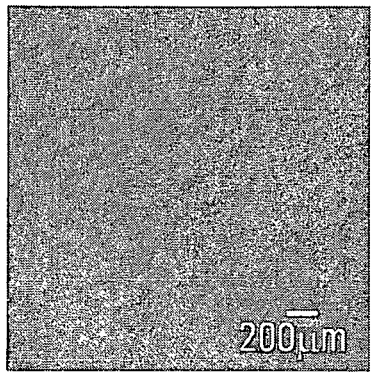
FIGS. 5A, 5B, 5C, 5D, 5E, 5F, 6A, 6B, 6C, 6D, 6E and 6F are confocal images depicting the phase separated structures of the Gtn-HPA/HA-Tyr composite hydrogels of FIGS. 1 and 2, taken at different concentrations of HRP.
Figure 5B:
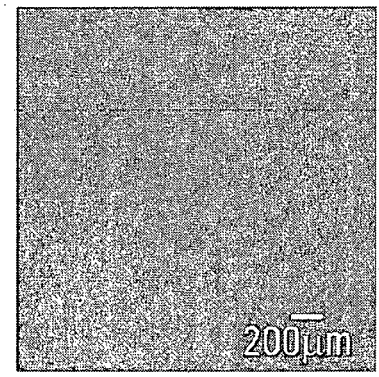
Figure 5C:
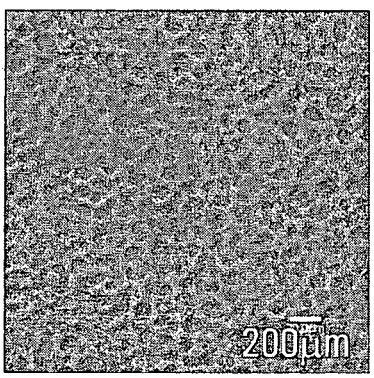
Figure 5D:
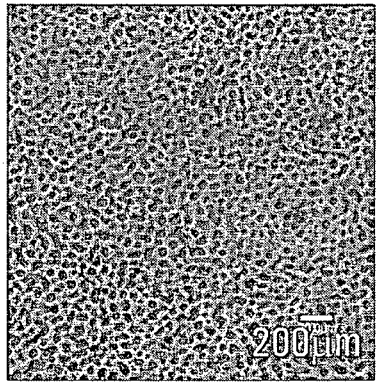
Figure 5E:
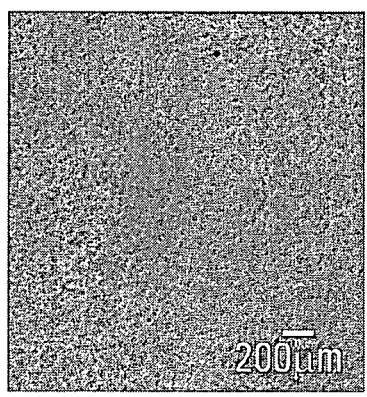
Figure 5F:
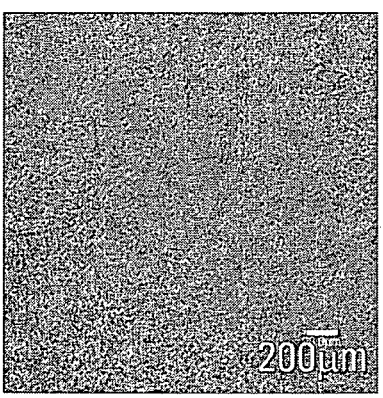
Figure 6A:
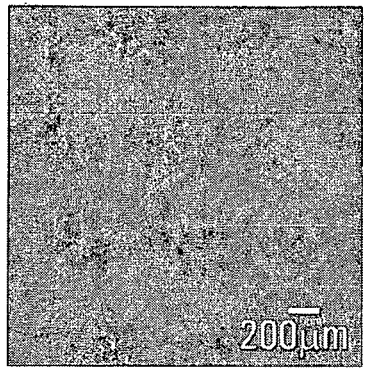
Figure 6B:
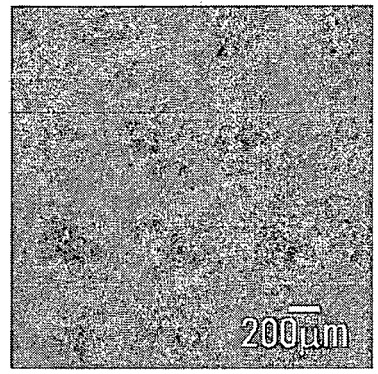
Figure 6C:
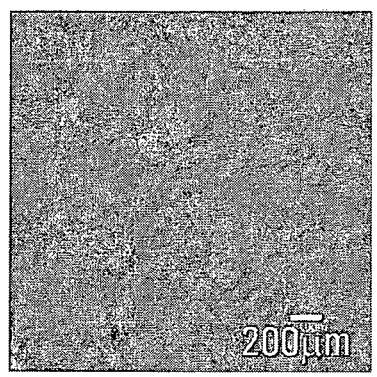
Figure 6D:
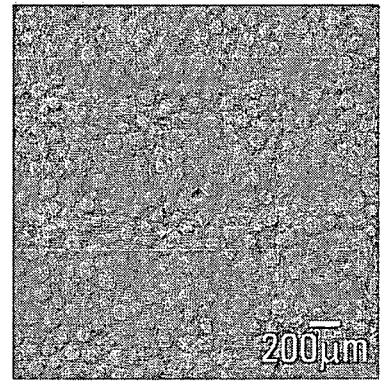
Figure 6E:
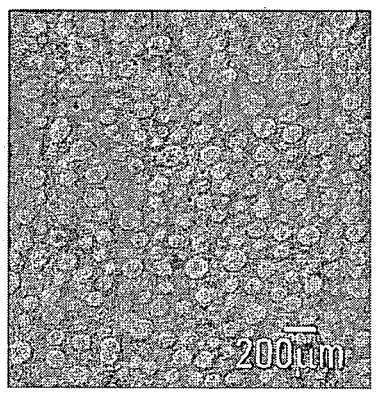
Figure 6F:
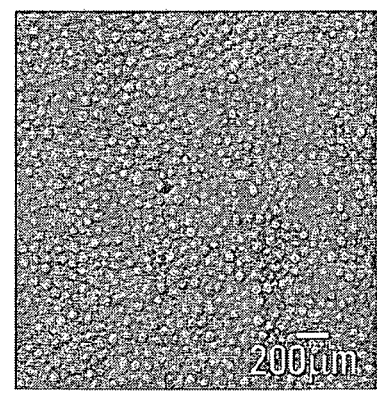
Figure 7A:
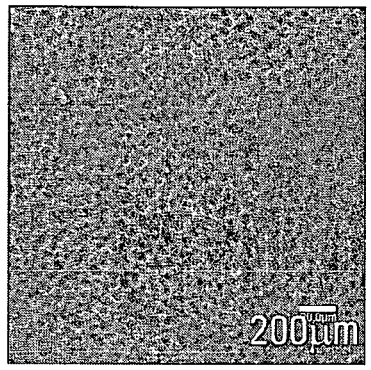
FIGS. 7A, 7B, 7C, 7D, 7E, 8A, 8B, 8C, 8D, 8E and 8F are confocal images depicting the phase separated structures of the Gtn-HPA/HA-Tyr composite hydrogels of FIGS. 3 and 4, taken at different concentrations of HRP.
Figure 7B:
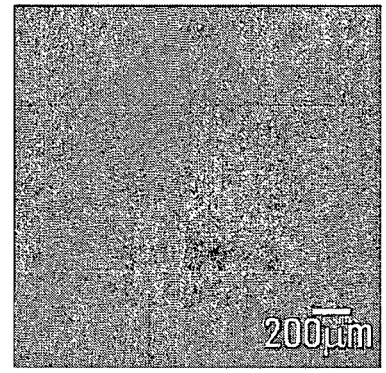
Figure 7C:
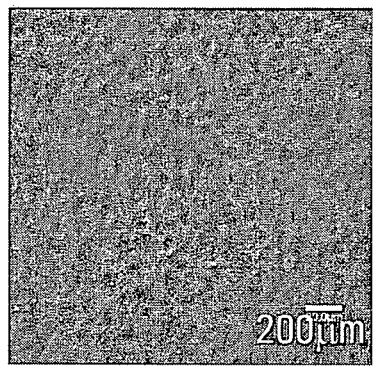
Figure 7D:
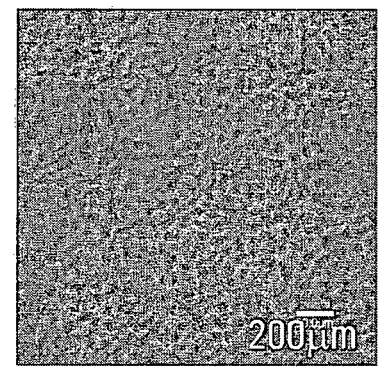
Figure 7E:
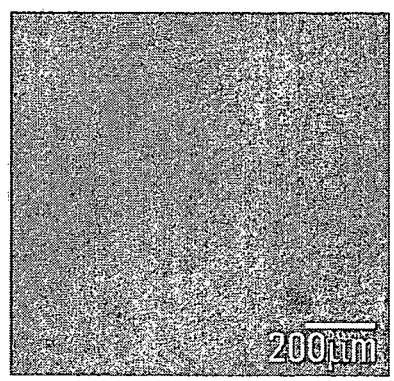
Figure 8A:
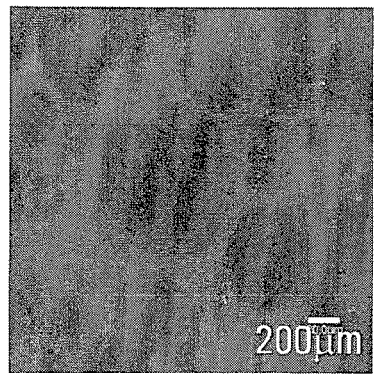
Figure 8B:
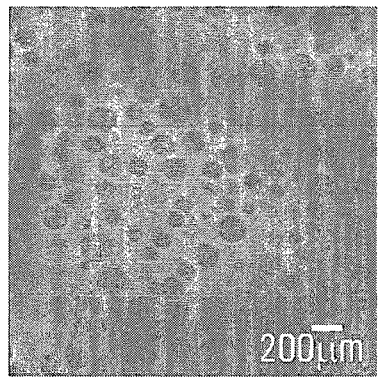
Figure 8C:
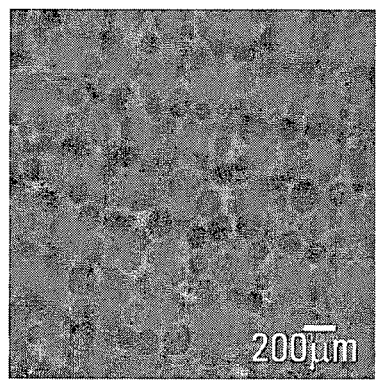
Figure 8D:
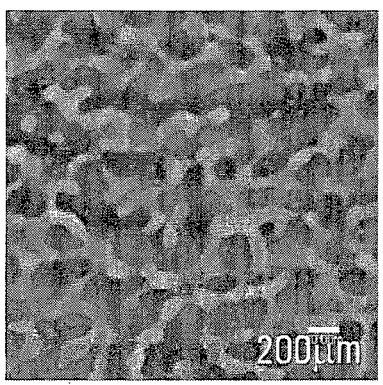
Figure 8E:
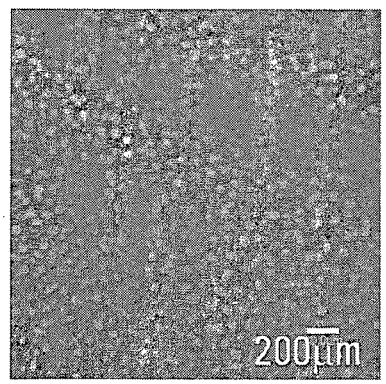
Figure 8F:
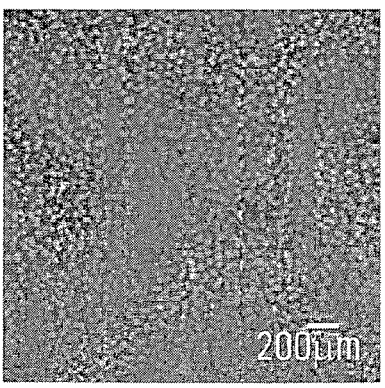

FIG. 3 shows the dependency of stiffness of Gtn-HPA/HA-Tyr composite gels on HRP concentration, which is indicated by the G' values of sample IV-3 and sample IV-4 as a function of HRP concentration at a fixed $H_2O_2$ concentration of 17 mM. FIG. 4 shows the dependency of gelation time of Gtn-HPA/HA-Tyr composite gels on HRP concentration, which is indicated by the gelation time of sample IV-3 and sample IV-4 as a function of HRP concentration at a fixed $H_2O_2$ concentration of 17 mM.

As can be seen from FIGS. 1 and 3, at a fixed HRP and $H_2O_2$ concentration, the addition of the HA-Tyr conjugate to the Gtn-HPA conjugate resulted in a lower G' value for the Gtn-HPA/HA-Tyr composite hydrogel when compared to that for the Gtn-HPA hydrogel alone. In addition, the G' value of the composite hydrogel increased with an increase in the HRP concentration from 0.02 units/ml to 0.2 units/ml.

As shown in FIGS. 2 and 4, at a fixed HRP and $H_2O_2$ concentration, the gelation time of the Gtn-HPA/HA-Tyr composite hydrogel increased with an increase in the percentage of the HA-Tyr. Further, these results show that the gelation time was generally longer with a decrease in the HRP concentration at a fixed $H_2O_2$ concentration.

Accordingly, as can be understood from FIGS. 1, 2, 3 and 4, at a fixed $H_2O_2$ concentration, a higher HRP concentration yielded a Gtn-HPA/HA-Tyr composite hydrogel with higher stiffness and less gelation time, although the overall stiffness of the composite gel was lower when $H_2O_2$ was kept at 17 mM compared to when $H_2O_2$ was kept at 8.5 mM.

Example V Confocal Images of Phase-Separated Gtn-HPA/HA-Tyr Composite Hydrogels

Solutions of Gtn-HPA-Rho and HA-Tyr-Flu, as prepared in Examples I-B and III respectively, were prepared by dissolving the respective conjugates in phosphate buffered saline (PBS, pH=7.4), wherein the final concentration of each of the Gtn-HPA-Rho and HA-Tyr-Flu solutions was 5 wt %. Aqueous solutions containing Gtn-HPA-Rho and HA-Tyr-Flu in the ratio of 9:1 or 8:2 were prepared (5 wt %, 250 µL PBS). The Gtn-HPA-Rho solution was mixed with the HA-Tyr-Flu solution.

In a representative confocal image measurement, a solution of HRP in PBS and a solution of $H_2O_2$ in PBS were added sequentially to an aqueous solution containing Gtn-HPA-Rho and HA-Tyr-Flu, prepared according to the above paragraph, to form a sample solution. The sample solution was then vortexed and immediately transferred into a 96-well plate. The composite hydrogels were allowed to set overnight in the dark, followed by soaking in PBS (PH=7.4) for 4 hours before being imaged with a confocal laser scanning microscopy (Olympus™ FV300, Japan).

The confocal image measurements were repeated, wherein the concentration of HRP ranged from 0.02 units/ml to 0.2 units/ml and the concentration of $H_2O_2$ was either 8.5 mM or 17 mM.

FIGS. 5A, 5B, 5C, 5D, 5E, 5F, 6A, 6B, 6C, 6D, 6E, 6F, 7A, 7B, 7C, 7D, 7E, 8A, 8B, 8C, 8D, 8E and 8F show the respective confocal fluorescence images of the phase separated structures of sample IV-1, sample IV-2, sample IV-3 and sample IV-4 at various HRP concentrations: A) 0.02 units/ml, B) 0.024 units/ml, C) 0.032 units/ml, D) 0.045 units/ml, E) 0.05 units/ml and F) 0.1 units/ml. Gtn-HPA and HA-Tyr phases were detected in red and green, respectively. As can be seen from these figures, the average size of the discrete regions ranged from about 0.01 µm to about 50 µm and the average distance between adjacent regions ranged from about 0.01 µm to about 50 µm.

As can be shown in FIGS. 5A, 5B, 5C, 5D, 5E, 5F, 6A, 6B, 6C, 6D, 6E, 6F, 7A, 7B, 7C, 7D, 7E, 8A, 8B, 8C, 8D, 8E and 8F, the Gtn-HPA phase separated and formed varied patterns with various concentrations of HRP when the concentration of $H_2O_2$ was fixed at either 8.5 mM or 17 mM.

In the case of sample IV-1 (concentration of $H_2O_2$=8.5 mM), the Gtn-HPA phase appeared as a mesh network while the HA-Tyr phase appeared as spheres dispersed throughout the composite hydrogel sample (see FIGS. 5A, 5B, 5C, 5D, 5E, 5F). The phase separation degree was lower with increased HRP concentration.

In contrast, in the case of sample IV-2 (concentration of $H_2O_2$=8.5 mM), the Gtn-HPA phase appeared as spheres while the HA-Tyr phase appeared as a mesh network (FIGS. 6A, 6B, 6C, 6D, 6E, 6F). The higher concentrations of HRP resulted in a smaller size of the Gtn-HPA phase as particles. This observation seemed to be in good correlation with the gelation time of the composite hydrogels.

Phase-separated structures were also observed in samples IV-3 and IV-4, both of which were prepared using 17 mM $H_2O_2$. The morphology of sample IV-3 (FIGS. 7A, 7B, 7C, 7D, 7E) showed a similar trend as that of sample IV-1 (FIGS. 5A, 5B, 5C, 5D, 5E, 5F). However, in the case of sample IV-4 (FIGS. 8A, 8B, 8C, 8D, 8E, 8F), the Gtn-HPA phase transited from a mesh network to spheres with increasing HRP concentration.

Example VI Gtn-HPA/HA-Tyr Composite Hydrogels Containing HFF1

HFF1 proliferation in sample Gtn-HPA/HA-Tyr composite hydrogels with different microstructures was studied.

Freeze dried Gtn-HPA and HA-Tyr were prepared according to the procedures described in Examples I-A and II above.

7.5% Gtn-HPA and 7.5% HA-Tyr solutions were made by dissolving freeze dried Gtn-HPA and HA-Tyr respectively in phenol-red free DMEM supplemented with 10% FBS, 100 units/ml of penicillin and 100 mg/ml of streptomycin. 7.5% Gtn-HPA/HA-Tyr composite hydrogel solution, comprising Gtn-HPA and HA-Tyr in a weight ratio of 8:2, were prepared with 0.175 mM of $H_2O_2$ and HRP at the concentration of 0.0199 units/ml, 0.0437 units/ml and 0.0596 units/ml according to the procedure described in Example IV above. The resulting Gtn-HPA/HA-Tyr composite hydrogels were samples VI-1, VI-2 and VI-3 respectively. HFF1 in an appropriate volume of phenol-red free DMEM was added to each of the 7.5% Gtn-HPA/HA-Tyr composite hydrogel solution so as to dilute each composite hydrogel solution into 5% Gtn-HPA/HA-Tyr composite hydrogel solution with HFF1 at a density of 220,000 cells/ml.

50 μl droplets of the 5% composite hydrogel solutions containing HFF1 prepared above were transferred under sterile conditions in a 48-well plate (Nunc™, Denmark) and were left to gel overnight in a cell incubator at 37° C. with 5% $CO_2$ and 95% humidity. The next day, fresh DMEM was added to each well. The culture medium was changed every 2 days.

HFF1 proliferation was analyzed weekly for 4 weeks to assess their proliferation using Quant-iT™ PicoGreen dsDNA Kit (Invitrogen™) seeded in each composite hydrogel. At the end of each week, the composite hydrogels containing HFF1 were dissolved using 0.5 mg/ml colleagenase and were centrifuged for 5 minutes at 1500 rpm. Supernatants were removed and 200 μl of reporter lysis buffer was added to each composite hydrogel containing HFF1. Each of the resulting cell mixture was votexed for 30 seconds, stored at −20° C., thawed and sonicated for 30 minutes on ice, and centrifuged at 6.0 rpm for 20 minutes at 4° C. Each of the resulting sample supernatants was collected and used for the PicoGreen DNA assay.

DNA standard (2 μg/ml) was prepared from 100 μg/ml of the DNA solution and 1× TE buffer. PicoGreen dsDNA Quantitation reagent was prepared by making a 1:200 dilution of the concentrated dye solution in 1× TE buffer. 100 μl of appropriately diluted sample supernatant was added into each well of a 96-well plate. Then, 100 μl of PicoGreen reagent was added to each well. The samples were excited at 480 nm and fluorescence intensity was measured at 520 nm using Tecan Infinite® M200 microplate reader. The fluorescence intensity is proportional to the number of HFF1. A DNA standard curve and a HFF1 standard curve were plotted. The number of cells that adhered on each composite hydrogel was calculated from the standard curves.

Figure 9A:
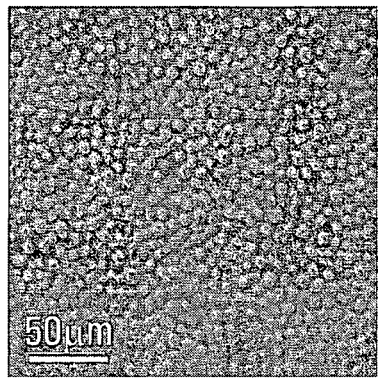
FIGS. 9A, 9B and 9C are confocal images depicting the phase separated structures of different sample Gtn-HPA/HA-Tyr composite hydrogels.
Figure 9B:
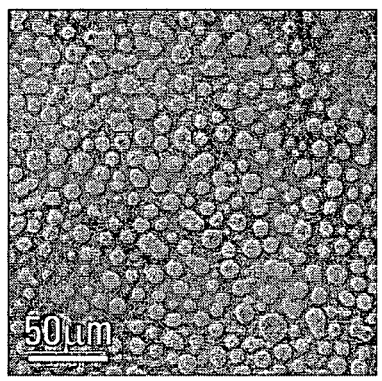
Figure 9C:
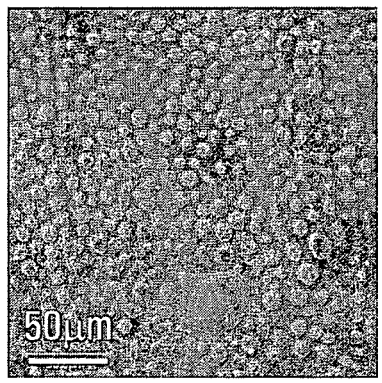

FIGS. 9A, 9B and 9C are confocal images, taken using a confocal laser scanning microscope (Olympus™ FV300, Japan), of the sample composite hydrogels showing that the average size of the discrete Gtn-HPA regions (stained red) increased with increasing HRP concentration: the concentration of HRP used for FIG. 9A, FIG. 9B and FIG. 9C were respectively 0.0199 units/ml, 0.0437 units/ml and 0.0596 units/ml. Prior to taking the confocal images, the Gtn-HPA was conjugated with Rhodamine in accordance with the procedure described in Example I-B above, while the HA-Tyr portion was conjugated with FITC in accordance with the procedure described in Example III above.

Figure 10:
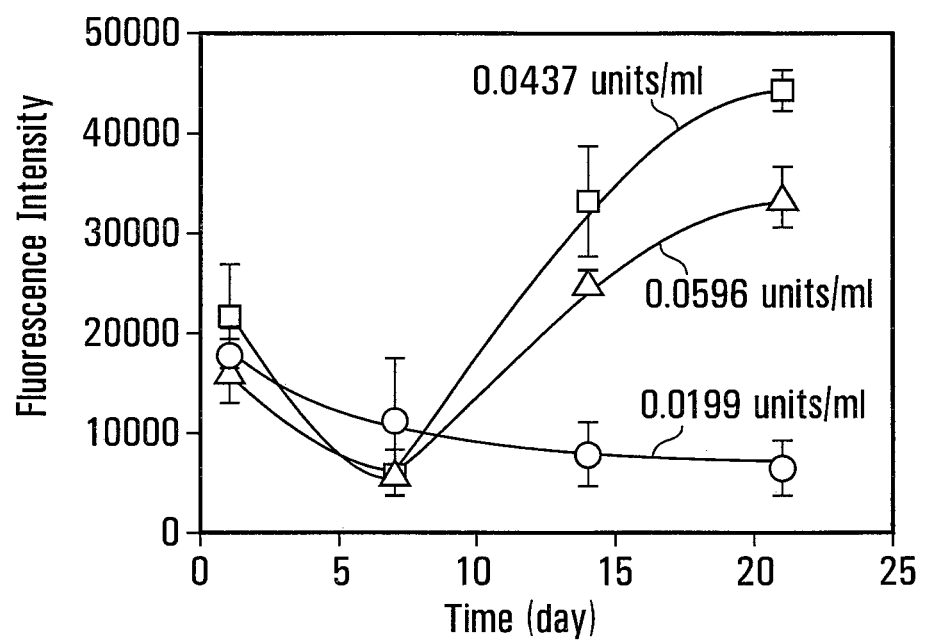
FIG. 10 is a line graph of cell growth over time on the different sample Gtn-HPA/HA-Tyr composite hydrogels of FIGS. 9A, 9B and 9C.

FIG. 10 shows the dependency of HFF1 proliferation on the average size of discrete Gtn-HPA regions. It was observed that more HFF1 adhered to larger discrete Gtn-HPA regions.

Example VII: Gtn-HPA/HA-Tyr Composite Hydrogels and Primary Rat Hepatocytes' Albumin Secretion Effect of composition of sample Gtn-HPA/HA-Tyr composite hydrogels on primary rat hepatocytes' albumin secretion was studied.

5% Gtn-HPA and 5% HA-Tyr solutions were made by dissolving freeze dried Gtn-HPA and HA-Tyr, prepared in accordance with the procedures in Example I-A and II above, respectively in phenol-red and FBS free Hepatozyme media (Invitrogen) supplemented with 0.1 mM of dexamethasone (Sigma), 100 units/ml of penicillin and 100 mg/ml of streptomycin (Invitrogen). Sample Gtn-HPA/HA-Tyr composite hydrogel solutions with different compositions of Gtn-HPA and HA-Tyr but the same stiffness (G'=690 Pa, 1340 Pa or 3340 Pa) were prepared by adding 0.88 mM of $H_2O_2$ and varying amounts HRP respectively, in accordance with the procedure described in Example IV above and the ingredients are summarized in TABLE II.

TABLE II

Sample Gtn-HPA/HA-Tyr composite hydrogels (samples VII-1A, VII-1B, VII-1C, VII-2A, VII-2B, VII-2C, VII-3A, VII-3B and VII-3C)

| Gtn-HPA:HA-Tyr (wt. ratio) | [HRP] (units/ml) (sample 3) (FIG. #) | | |
|---|---|---|---|
| | G' = 690 Pa | G' = 1340 Pa | G' = 3340 Pa |
| 10:0 | 0.0477 (VII-1A) | 0.0581 (VII-1B) | 0.0894 (VII-1C) |
| 8.5:1.5 | 0.0388 (VII-2A) (FIG. 11A) | 0.0496 (VII-2B) (FIG. 11B) | 0.135 (VII-2C) (FIG. 11C) |
| 7:3 | 0.0596 (VII-3A) (FIG. 11D) | 0.0993 (VII-3B) (FIG. 11E) | 0.198 (VII-3C) (FIG. 11F) |

Sample Gtn-HPA/HA-Tyr composite hydrogel solutions (250 μl per well) were deposited under sterile conditions in a 48-well plate and left to gel overnight in a cell incubator at 37° C. Primary rat hepatocytes were seeded at 10,000 cells per well and then incubated at 37° C. with 5% $CO_2$ and 95% humidity. After 12 hours of incubation, unattached hepatocytes were washed off by PBS and fresh culture medium was added. Culture medium was changed and collected every 24 hours to assess the amount of albumin secreted, using the rat albumin enzyme linked immunosorbent assay (ELISA) quantitation kit from Immunology Consultants Laboratory (ICL).

FIGS. 11A, 11B, 11C, 11D, 11E and 11F are confocal images, taken using a confocal laser scanning microscope (Olympus™ FV300, Japan), of sample composite hydrogels VII-2A, VII-2B, VII-2C, VII-3A, VII-3B and VII-3C. Prior to taking the confocal images, the Gtn-HPA in each sample was conjugated with Rhodamine in accordance with the procedure described in Example I-B above and appeared in red, while the HA-Tyr in each sample was conjugated with FITC in accordance with the procedure described in Example III above and appeared in green.

It was observed from FIGS. 11A, 11B, 11C, 11D, 11E and 11F that at a fixed Gtn-HPA and HA-Tyr composition, the degree of phase separation in the sample composite hydrogels decreased with increasing concentration of HRP from 0.0388 units/ml to 0.135 units/ml. In addition, when the weight ratio Gtn-HPA:HA-Tyr=8.5:1.5, the Gtn-HPA phase appeared as a matrix network while the HA-Tyr phase appeared as domains, and the Gtn-HPA matrix network became denser with increasing HRP concentration (FIGS. 11A, 11B, and 11C). When the weight ratio Gtn-HPA:HA-Tyr=7:3, the Gtn-HPA phase appeared as domains while the HA-Tyr phase appeared as a matrix network, and the Gtn-HPA domains became smaller with increasing HRP concentration (FIGS. 11D, 11E, and 11F).

Figure 12:
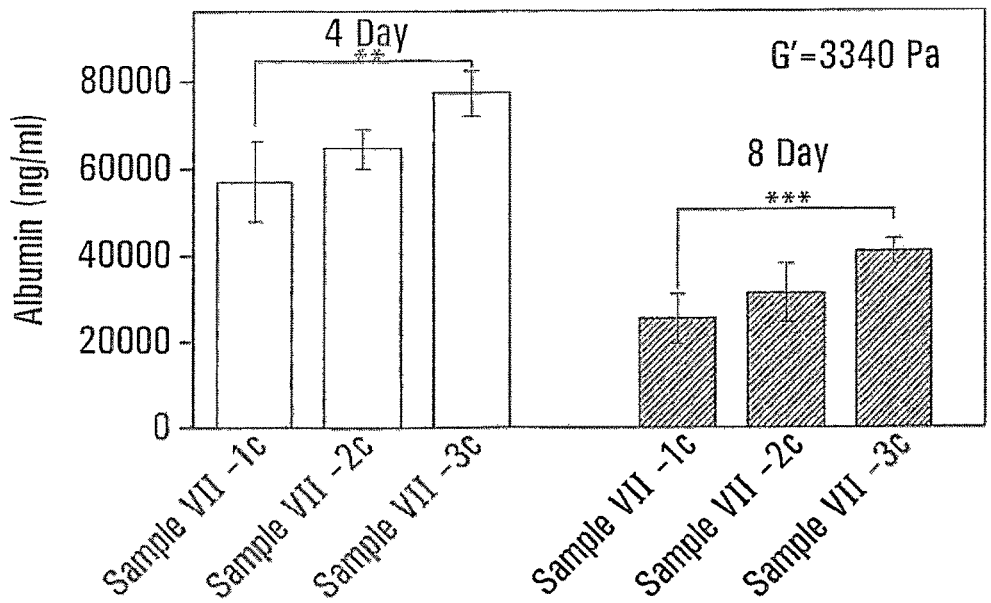
FIG. 12 is a bar graph depicting albumin production by hepatocytes on the different sample Gtn-HPA/HA-Tyr composite hydrogels of FIGS. 11C and 11F.

FIG. 12 depicts albumin secretion by primary rat hepatocytes sample composite hydrogels VII-2C and VII-3C as compared with sample Gtn-HPA hydrogel VII-1C at 4 days and 8 days, when G'=3340 Pa (t test: p<0.0002; *p<0.002). It was observed that at a given G' (i.e. stiffness), a higher amount of HA-Tyr in the composite hydrogels (sample VII-3C v. sample VII-2C) enhanced albumin secretion by hepatocytes. It was also observed that each of the composite hydrogels (samples VII-2C and VII-3C) led to more albumin secretion by hepatocytes as compared to Gtn-HPA hydrogel alone (sample VII-1C), suggesting that the Gtn-HPA/HA-Tyr composite hydrogels were better at maintaining hepatocyte function, as compared to the pure Gtn-HPA hydrogel.

Comparative Example: Gtn-HPA Hydrogels Containing Primary Rat Hepatocytes' Albumin Secretion Effect of stiffness (indicated by the G' value) of Gtn-HPA hydrogels on primary rat hepatocytes' albumin secretion was studied.

5% Gtn-HPA was made by dissolving freeze dried Gtn-HPA prepared in accordance with the procedure in Example I-A above, in phenol-red free Hepatozyme media supplemented with 10% FBS, 0.1 mM of dexamethasone (Sigma™), 100 units/ml of penicillin and 100 mg/ml of streptomycin. Gtn-HPA solutions with G'=231 Pa and 2118 Pa were prepared by adding 0.88 mM of $H_2O_2$ and 0.0198 units/ml and 0.0356 units/ml of HRP respectively. The Gtn-HPA hydrogels were prepared under sterile conditions in a 48-well plate and left to gel overnight in the incubator at 37° C. 250 µl of gel was added to each well. Next, hepatocytes were seeded at 10,000 cells per well and then incubated at 37° C. with 5% $CO_2$ and 95% humidity. After 12 hours, unattached hepatocytes were washed off by PBS and fresh culture medium was added. Culture medium was changed and collected every 24 hours to assess the amount of albumin produced, using the rat albumin enzyme linked immunosorbent assay (ELISA) quantitation kit from Immunology Consultants Laboratory (ICL).

Figure 13:
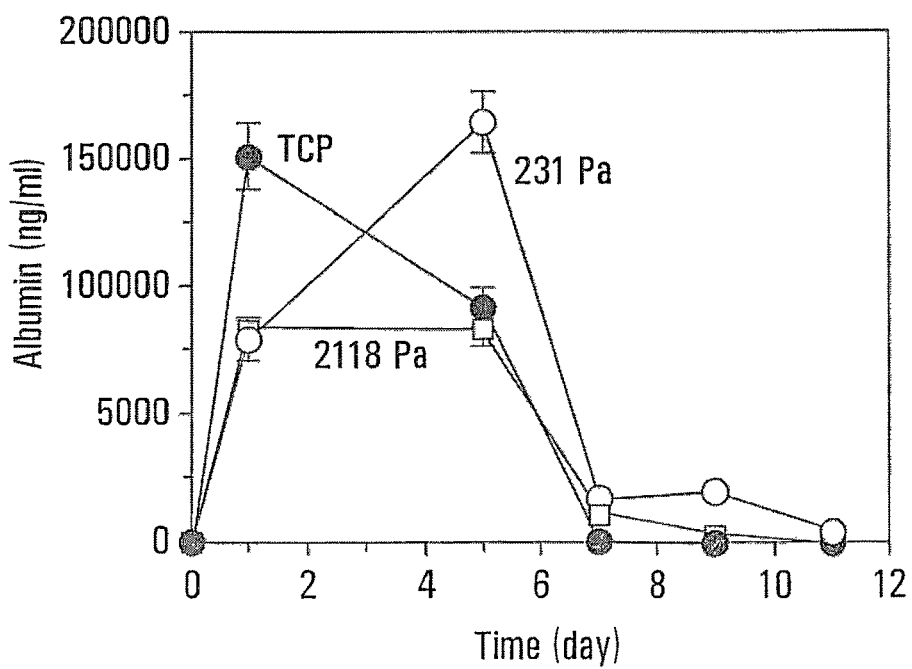
FIG. 13 is a line graph depicting albumin production by hepatocytes over time on different sample Gtn-HPA hydrogels (for comparison).

FIG. 13 shows the dependency of albumin secretion on the stiffness of the Gtn-HPA hydrogels. It was observed that the Gtn-HPA hydrogels were better substrates for hepatocyte growth as compared to the tissue culture plate (TCP) control. In addition, hepatocytes were able to maintain their functionality for longer periods when grown on softer Gtn-HPA hydrogels (G'=231 Pa), as compared to stiffer Gtn-HPA hydrogels (G'=2118 Pa).

It will be understood that any range of values herein is intended to specifically include any intermediate value or sub-range within the given range, and all such intermediate values and sub-ranges are individually and specifically disclosed.

It will also be understood that the word "a" or "an" is intended to mean "one or more" or "at least one", and any singular form is intended to include plurals herein.

It will be further understood that the term "comprise", including any variation thereof, is intended to be open-ended and means "include, but not limited to," unless otherwise specifically indicated to the contrary.

When a list of items is given herein with an "or" before the last item, any one of the listed items or any suitable combination of two or more of the listed items may be selected and used.

Of course, the above described embodiments are intended to be illustrative only and in no way limiting. The described embodiments are susceptible to many modifications of form, arrangement of parts, details and order of operation. The invention, rather, is intended to encompass all such modification within its scope, as defined by the claims.

What is claimed is:

1. A composite comprising:
    a first conjugate of a polymer and a first phenol-containing moiety; and
    a second conjugate of a gelatin or collagen and a second phenol-containing moiety;
    wherein said polymer is selected so that said first conjugate is less cell-adhesive than said second conjugate, at least one of said first and second conjugates is cross-linked to form a matrix, and said composite comprises discrete regions that are rich in one of said first and second conjugates, wherein said composite has a storage modulus of about 4 kPa or less, and wherein the discrete regions have an average size of about 10 nm to about 500 µm, where the discrete regions reflect the degree of phase separation in the composite;
    wherein the composite includes phase separation, and the composite comprises a first phase formed of the first conjugate and a second phase formed of the second conjugate.

2. The composite of claim 1, wherein said composite is a composite hydrogel.

3. The composite of claim 1, wherein said polymer comprises a hyaluronic acid, a poly(ethylene glycol), or a dextran.

4. The composite of claim 1, wherein at least one of said first phenol-containing moiety and said second phenol-containing moiety comprises tyramine or a hydroxyphenylpropionic acid.

5. The composite of claim 1, wherein said second conjugate comprises said gelatin.

6. The composite of claim 1, wherein said second conjugate comprises a conjugate of said gelatin and tyramine, and a conjugate of said gelatin and hydroxyphenylpropionic acid.

7. The composite of claim 1, wherein said first conjugate comprises a conjugate of said polymer and tyramine, and a conjugate of said polymer and hydroxyphenylpropionic acid.

8. The composite of claim 1, wherein said discrete regions are rich in said second conjugate.

9. The composite of claim 1, wherein an average distance between adjacent discrete regions is from about 5 nm to about 500 µm.

10. The composite of claim 1, wherein said first conjugate is nonadhesive to cells.

11. A method of forming the composite of claim 1, comprising:
    mixing precursors for the first and second conjugates in a solution for forming said composite; and
    dispersing a catalyst in said solution to catalyze crosslinking of at least one of said first and second conjugates to form the matrix.

12. The method of claim 11, wherein said catalyst is dispersed in said solution in an amount selected to control a rate of said crosslinking to allow one of said first and second conjugates to concentrate in discrete regions having sizes in a pre-selected range.

13. The method of claim 11, wherein said catalyst comprises at least one of horseradish peroxidase and $H_2O_2$.

14. The method of claim 11, wherein said catalyst comprises horseradish peroxidase and $H_2O_2$.

15. The method of claim 14, wherein the concentration of horseradish peroxidase in said solution is selected to control said rate of crosslinking.

16. The method of claim 14, wherein the concentration of $H_2O_2$ in said solution is selected to control stiffness of said composite.

17. A composite comprising:
    a polymer; and
    a gelatin or collagen;
    wherein at least one of said polymer and said gelatin or collagen is conjugated with a phenol-containing moiety, said polymer is less cell-adhesive than said gelatin or collagen, said at least one of said polymer and said gelatin or collagen is crosslinked to form a matrix, and said composite comprises discrete regions that are rich in one of said polymer and said gelatin or collagen, wherein said composite has a storage modulus of about 4 kPa or less, where the discrete regions reflect the degree of phase separation in the composite;
    wherein the composite includes phase separation, and the composite comprises a first phase formed of the first conjugate and a second phase formed of the second conjugate.

18. A method of forming the composite of claim 17, comprising:
    mixing said polymer and said gelatin or collagen in a solution for forming said composite, wherein the at least one of said polymer and said gelatin or collagen is conjugated with said phenol-containing moiety; and
    dispersing a catalyst in said solution to catalyze crosslinking of at least one of said polymer and said gelatin or collagen to form the matrix.

19. The composite of claim 1, wherein said composite has a storage modulus in the range of about 0.2 kPa to about 4 kPa.

20. A composite comprising:
    a first conjugate of a polymer and a first phenol-containing moiety; and
    a second conjugate of a gelatin or collagen and a second phenol-containing moiety;
    wherein said polymer is selected so that said first conjugate is less cell-adhesive than said second conjugate, at least one of said first and second conjugates is crosslinked to form a matrix, and said composite comprises discrete regions that are rich in one of said first and second conjugates, wherein said discrete regions have an average size of about 10 nm to about 500 µm where the discrete regions reflect the degree of phase separation in the composite;
    wherein the composite includes phase separation, and the composite comprises a first phase formed of the first conjugate and a second phase formed of the second conjugate.

* * * * *